United States Patent
Baumeister

(12) 
(10) Patent No.: US 6,376,239 B1
(45) Date of Patent: Apr. 23, 2002

(54) DNA MOLECULES COMPRISING A PROMOTER CAPABLE OF CONFERRING EXPRESSION OF A HETEROLOGOUS DNA SEQUENCE

(75) Inventor: Ralf Baumeister, Gröbenzell (DE)

(73) Assignee: EleGene GmbH, Martinsreid (DE)

( * ) Notice: Subject to any disclaimer, the term of this patent is extended or adjusted under 35 U.S.C. 154(b) by 0 days.

(21) Appl. No.: 08/832,867

(22) Filed: Apr. 4, 1997

(51) Int. Cl.[7] .......................... C07H 21/00; C12N 1/11; C12N 5/10; C12N 15/12

(52) U.S. Cl. .................... 435/325; 435/325; 435/252.3; 435/254.11; 435/320.1; 536/23.1; 536/23.5; 536/24.1

(58) Field of Search .............................. 435/69.1, 320.1, 435/325, 440, 455, 252.3, 254.11; 514/44; 536/73.1, 23.5, 24.1; 800/3, 8, 9

(56) References Cited

U.S. PATENT DOCUMENTS 5,840,540 A * 11/1998 St. George-Hyslop et al. .. 435/69.1

FOREIGN PATENT DOCUMENTS

EP 0274826 * 7/1988

OTHER PUBLICATIONS

Orkin and Motulsky, in Report and Recommendations Of The Panel To Assess The NIH Investment In Research On Gene Therapy, pp. 1–41, 1995.*

Rogaev et al., Nature, 376:775–778, 1995.*
Granato et al., Nucleic Acids Research, 22:1762–1763, 1994.*
Levitan et al., Proc. Natl. Acad. Sci., USA, 93:14940–14944, 1996.*
Li et al., Neuron, 17:1015–1021, 1996.*

* cited by examiner

*Primary Examiner*—Deborah Crouch
*Assistant Examiner*—Peter Brunouskis
(74) *Attorney, Agent, or Firm*—Peter F. Corless; Edwards & Angell, LLP

(57) ABSTRACT

Described and claimed are recombinant DNA molecules including the promoter region of the sel-12 gene of Caenorhabditis elegans (*C. elegans*) or promoter regions of genes homologous to the sel-12 gene, being capable of conferring expression of a heterologous DNA sequence in all neural cells, such as at all stages of development. Vectors including such recombinant DNA molecules are provided. Described and claimed also are pharmaceutical and diagnostic compositions as well as kits including the aforementioned recombinant DNA molecules and vectors. Furthermore, transgenic non-human animals, including the aforesaid recombinant DNA molecules or vectors stably integrated into their genome and their use for the identification of substances capable of complementing a neuronal disorder are described and claimed. Also provided are uses of the before described DNA molecules, vectors and substances for the preparation of a pharmaceutical composition for treating, preventing, and/or delaying a neuronal disorder in a subject. Furthermore, the use of the aforementioned DNA molecules and vectors for the preparation of pharmaceutical compositions for inducing a neuronal disorder in a non-human animal is described and claimed.

10 Claims, 57 Drawing Sheets

FIG. 3A (1) GENERAL INFORMATION:

(i) APPLICANT:

(A) NAME: Baumeister, Ralf
    (B) STREET: Freilandstr. 44a
    (C) CITY: Groebenzell
    (E) COUNTRY: Germany
    (F) POSTAL CODE (ZIP): 82194

(ii) TITLE OF INVENTION:

DNA MOLECULES COMPRISING A PROMOTER CAPABLE OF CONFERRING EXPRESSION OF A HETEROLOGOUS DNA SEQUENCE IN ALL NEURAL CELLS AT ALL STAGES OF DEVELOPMENT IN C.ELEGANS AND USES THEREOF

FIG. 3B (iii) NUMBER OF SEQUENCES: 8

(iv) COMPUTER READABLE FORM:

(A) MEDIUM TYPE: Floppy disk (B) COMPUTER: IBM PC compatible (C) OPERATING SYSTEM: PC-DOS/MS-DOS (D) SOFTWARE: PatentIn Release #1.0, Version #1.30 (EPO)

(2) INFORMATION FOR SEQ ID NO: 1:

(i) SEQUENCE CHARACTERISTICS:

(A) LENGTH: 4737 base pairs (B) TYPE: nucleic acid (C) STRANDEDNESS: single (D) TOPOLOGY: linear (ii) MOLECULE TYPE: DNA (genomic)

(iv) ANTI-SENSE: NO (xi) SEQUENCE DESCRIPTION: SEQ ID NO: 1:

TGAAAGTTGT ATTAAGATTT ACAGCTGTGT CAGTGTCATT CAAAAACATT CCATACATT  60

TTCAAACCTT CCATAACATT TCACAATTTT CTAGAACGTC CTAAAAATGT CAGAAATTTG 120

CTGAAACTTC CGAAAACAGC CGGAAGTTTA CAAAAGCTCC CATACATTTT CAGAACTTAC 180

TTCAATATTC TCCATATCCA TATTTTTTAA AAATGGCTGT GCATTAAGCT CATCGTCTAT 240

FIG. 3C

```
TAAACTAAAA GAGGTCATAT TATATTTAGT TTCCAATGCC AAAAACTCCC TATCCCAGGT    300

TTTCACAAAA ATATGTGAAA GACTGAGGAA ATCTTAAAAA TAAACGTCCA ACTTTCATAG    360

CACCCCTCTG ATCTTTGACA ATTTTTTAGA TAGAGCTAAA GATATATTACTG AAAACATTTT  420

ATGATGGTTT TTTAAAATTA TGTATGTTTT CATGTCTGAG TTACTAGTTT TCCATTACAA    480

AAACTTAATT CTGATGTGAC ATTTATGAAA ATTGCCGACC ATTGCAATAA AAAGACACAA    540

TAATTTGAAT AACAATGACC TCAATATGAT AACATTTCA AGGAGGCTAT AGCAAAAACG     600

TTATTGTCGT TATACAGGAT CACTAGCTCA GTGCATTTAA TAGTTGGTCA GTGACTTTAT    660

TTTCAGTCA GTGCGCACAT CTCGCCCCAT GTTCCATACT GGCAATCTGC ACTCAACAGT    720
```

FIG. 3D

```
TTTATTCTTC ATTAATGCAC GTAAACAAAT GATGACGGCC CGACTCGTTG AAAAGGGATA    780

CCTCCTATTT CTCTACTACC TCTACTCTCT ATACCCTCCT TCTTGGCCGC GGACTAGGTT    840

TCCTCTCTCCT CCTTTTCACC CTGCTCAGGG TTGACACACT TTATCGATTC TATTAATTAG   900

CTCTTTCACC TTTTTGTGA CATTTTTAAA TATTAAATTA AGTTATTGA ACGTTTCAGA     960

TGCCTTCCAC AAGGAGACAA CAGGAGGGCG GAGGTGCAGA TGCGGAAACA CATGTAAGTT   1020

ATTAGACAT TTTATTTTC TCAAGAACTA AATTGTTAAA ATTGCTACAA TGCATTGTTT    1080

CAGACCGTTT ACGGTACAAA TCTGATAACA AATCGGAATA GCCAAGAAGA CGAAAATGTT   1140

GTGGAAGAAG CGGAGCTGAA ATACGGAGCA TCTCACGTTA TTCATCTATT TGTGCCGGTG  1200
```

FIG. 3E

| | | | |
|---|---|---|---|
| TCACTATGCA | TGGCTCTGGT | TGTTTTTACG | ATGAACACGA | TTACGTTTTA | TAGTCAAAAC | 1260 |
| AATGGAAGGC | ATTTGTAAGT | TTTCTAAAGA | ATTGATTGAT | TAAAAATATT | TGATTTGTTT | 1320 |
| TATCAATTTG | CATCTGTGCA | ATCGCACTCT | TTGTCAGTGC | AAAATAATTT | TTGGTCAGTG | 1380 |
| CAAAATAATT | TTTGGTCAGT | GCATTGGTAT | TATGGTCAGT | GCATTTGCAA | GTCTGAGCTT | 1440 |
| TAACTATTTT | CGTGGTTTTA | ATTTTACTCA | ATTTTCTATC | AATATTTCTT | TGGAAAAAAG | 1500 |
| TTGAAGATTT | ACTCTGGAAA | TTTCGAAATA | AACTGTAAAT | GGAAAAATCA | ATCAACACAA | 1560 |
| ACTTTGAATT | ATTTTCAGAC | TATACACTCC | TTTTGTCCGG | GAAACAGACA | GTATCGTTGA | 1620 |
| GAAGGGATTG | ATGTCACTTG | GAAATGCTCT | CGTCATGTTG | TGCGTGGTCG | TTCTGATGAC | 1680 |

FIG. 3F

```
AGTTCTGCTG ATTGTTTTCT ATAAATACAA GTTTTATAAG CTTATTCATG GATGGCTTAT    1740

TGTCAGCAGT TTCTTCTTC TTTCCTATT CACTACAATC TATGTGCAGT AAGTTGATAT    1800

ATTACTATTC TCATAAAAAT ATCAATGTTG CAGAGAAGTT CTGAAAAGTT TCGATGTGTC    1860

TCCCAGCGCA CTATTGGTTT TGTTTGGACT GGGTAACTAT GGAGTTCTCG GAATGATGTG    1920

TATACATTGG AAAGGTCCAT TGCGTCTGCA ACAGTTCTAC CTTATTACAA TGTCTGCACT    1980

AATGGCTCTG GTCTTTATCA AGTACCTACC AGAATGGACT GTGTGGTTTG TGCTGTTTGT    2040

TATCTCGGTT TGGGATCTGG CACACCAAAA GGACCATTGA GATATTGGT    2100

GGAAACTGCA CAGGAGAGAA ACGAGCCAAT TTTCCCGGCG CTGATTTATT CGTGTAAGTT    2160
```

FIG. 3G

```
TCCTAATTTA TGGAATTAAT ATTCATGACG TTTCAAATTC TAAAACATTT TCAGCTGGAG    2220

TCATCTATCC CTACGTTCTT GTTACTGCAG TTGAAAACAC GACAGACCCC CGTGAACCGA    2280

CGTCGTCAGA CTCAAATAGT GAGTATCACC TAAAATTTTC GAATTTTTAT TCCAAAACTA    2340

ATTCAGCTT CTACAGCTTT TCCTGGAGAG GCGAGTTGTT CATCTGAAAC GCCAAAACGG     2400

CCAAAAGTGA AACGAATTCC TCAAAAAGTG CAAATCGAAT CGAATACTAC AGCTTCAACG    2460

ACACAAAACT CTGGAGTAAG GGTGGAACGG GAGCTAGCTG CTGAGAGACC AACTGTACAA    2520

GACGCCAATT TTCACAGGCA CGAAGAGGAA GAGAGTGAGT GAAAAACGTG CTGAAAAAGG    2580

GCAAAAGGGG ATGTATTTTC GCAAATTTTA CTCGAACTTT CTCACTTCTA ACTCAAATGT    2640

TTTTCTTGA CAGCACAAAA CGAAAATATT GCCGTCTACG TTCGGTATCG AAATACCCCC    2700
```

FIG. 3H

| | | |
|---|---|---|
| TGCAATTTTC ATTCGTTTTT | TTTTCACTGT TTCAATTTTT | CTCAACTTTT GAAGAGCAAT | 2760 |
| GCCGCCCACT CAGCTGAATA | TATTTTGTTC ATTTAAAGTT | CAAAACTTTT CAGTTAATAG | 2820 |
| ATTCAAGAAA GATCTCAAAT | AAACTTGCAA GCTTGCCACT | TGCGCTAGTC ACGAAAAAAA | 2880 |
| GGATTCTTC AATAACCCTC | TGTTCATATT TTTTTTAACA | ATAATTTTTC ATCTCTTCAT | 2940 |
| ATTTTGATAT GTTTTGCAAC | AAAAAAATGA TTGCAGGAGG | TGTGAAACTT GGTCTGGGCG | 3000 |
| ACTTCATTTT CTACTCTGTT | CTCCTCGGCA AGGCTTCATC | GTACTTTGAC TGGAACACGA | 3060 |
| CTATCGCTTG TTATGTGGCC | ATTCTTATCG GTCTCTGCTT | CACTCTTGTC CTGCTCGCCG | 3120 |
| TCTTCAAACG AGCACTCCCG | GCTCTGCCAA TTTCCATTTT | CTCCGGACTC ATTTTTTACT | 3180 |

FIG. 31

```
TTTGTACCCG CTGGATCATC ACCCCATTTG TTACACAAGT CTCTCAAAAG TGTTTATTAT    3240

ATTAATTCTC TGTTTTTGCC ATTTCTTTGC ATCATCAACT TTTCGATTAT ATCTTGAGCG    3300

ATCTCAAAGC TTTATTTTAC ATACCTATTT ATTTTTGAAC TTTGTCATTT AAGTTATATA    3360

AATAATTTAT TAAACGTTTC TGCTATTTTT TTTTCATTAT TCTTGATCCT ATGCTTACAG    3420

GTGCTTCAGA TTCCTTTTTT GCTTTAGAAG TATCATCAAA GTGTTTATTT AAAGTATTTC    3480

AGATGTTTTC TTCACGTCAT ATTTTATCAA ACGTTCGTCC AATAATAAAG GTAAGTTAAG    3540

GTAAGTAGAC ATATTCAGTT CCAAAGTTGG AAAATTAGTG AAACAACATT TTTATAAAG    3600

TAGTTGAAAT ACATAGTGAA TTTCTTGTTA AATTAAAAAT GTAGCAGAAG TGGGATAAA    3660
```

FIG. 3J

```
TTAAAAATTT TACTTTCAGA ATCTAGACCT GACCAGAGGG TTTTCCGACA GGAAAACAAA    3720

ATATTTTGAC TTGAATGACC TTATCAAAAC TGTAAATGTT ACCTACAAGA CTGGAGTAAA    3780

CCTGGAGGAA ACCACAACTG TCGAGTCAAA ATATGTAGTA AGTTTTTTTG TTTTTTTTTT    3840

CAAAAAATTA ACCTTTAAAT TATTGCTTCA GGATGTCACA CCTTCATCAA ACACAAAGG     3900

AACCGTAGTG ACACTATCAG GATCACCTGG TACACATAAC GATTTAAGT  ACATGAAATC    3960

GTTTTTTGAG CAGAAGAAAA TTCGCTTAAT TTGCACCAAC TATCCCGGGT CGGAATTTGT    4020

AACGGGTGGC TTGCACAATA GTTATACAAA TCAAGATCGA AATTCGTACA TGAAAAGTTT    4080

AATGGAAACA CTGGAGTTGA AAAATGTAAA CCGACTTATT ATAATGGGAC ACTCGAG       4137
```

FIG. 3K (2) INFORMATION FOR SEQ ID NO: 2:

(i) SEQUENCE CHARACTERISTICS:

(A) LENGTH: 2764 base pairs (B) TYPE: nucleic acid (C) STRANDEDNESS: single (D) TOPOLOGY: linear

FIG. 4A

FIG. 4B (ii) MOLECULE TYPE: cDNA to mRNA (iv) ANTI-SENSE: NO (ix) FEATURE:
    (A) NAME/KEY: CDS
    (B) LOCATION:249..1652

(xi) SEQUENCE DESCRIPTION: SEQ ID NO: 2:

TGGGACAGGC AGCTCCGGGG TCCGCGGTTT CACATCGGAA ACAAAACAGC GGCTGGTCTG    60

GAAGGAACCT GAGCTACGAG CCGCGGCGGC AGCGGGGCGG CGGGGAAGCG TATACCTAAT   120

```
CTGGGAGCCT GCAAGTGACA ACAGCCTTTG CGGTCCTTAG ACAGCTTGGC CTGGAGGAGA    180

ACACATGAAA GAAAGAACCT CAAGAGGCTT TGTTTCTGT GAAACAGTAT TTCTATACAG    240

TTGCTCCA ATG ACA GAG TTA CCT GCA CCG TTG TCC TAC TTC CAG AAT GCA    290
         Met Thr Glu Leu Pro Ala Pro Leu Ser Tyr Phe Gln Asn Ala
          1               5                  10

CAG ATG TCT GAG GAC AAC CAC CTG AGC AAT ACT GTA CGT AGC CAG AAT    338
Gln Met Ser Glu Asp Asn His Leu Ser Asn Thr Val Arg Ser Gln Asn
15                  20                  25                  30

GAC AAT AGA GAA CGG CAG GAG CAC AAC GAC AGA CGG AGC CTT GGC CAC    386
Asp Asn Arg Glu Arg Gln Glu His Asn Asp Arg Arg Ser Leu Gly His
                35                  40                  45
```

```
CCT GAG CCA TTA TCT AAT GGA CGA CCC CAG GGT AAC TCC CGG CAG GTG     434
Pro Glu Pro Leu Ser Asn Gly Arg Pro Gln Gly Asn Ser Arg Gln Val
         50                      55                      60

GTG GAG CAA GAT GAG GAA GAT GAG GAG CTG ACA TTG AAA TAT GGC         482
Val Glu Gln Asp Glu Glu Asp Glu Glu Leu Thr Leu Lys Tyr Gly
                 65                      70                      75

GCC AAG CAT GTG ATC ATG CTC TTT GTC CCT GTG ACT CTC TGC ATG GTG     530
Ala Lys His Val Ile Met Leu Phe Val Pro Val Thr Leu Cys Met Val
         80                      85                      90

GTG GTC GTG GCT ACC ATT AAG TCA GTC AGC TTT TAT ACC CGG AAG GAT     578
Val Val Val Ala Thr Ile Lys Ser Val Ser Phe Tyr Thr Arg Lys Asp
         95                      100                     105                 110
```

```
GGG CAG CTA ATC TAT ACC CCA TTC ACA GAA GAT ACC GAG ACT GTG GGC    626
Gly Gln Leu Ile Tyr Thr Pro Phe Thr Glu Asp Thr Glu Thr Val Gly
            115                     120                     125

CAG AGA GCC CTG CAC TCA ATT CTG AAT GCT GCC ATC ATG ATC AGT GTC    674
Gln Arg Ala Leu His Ser Ile Leu Asn Ala Ala Ile Met Ile Ser Val
            130                     135                     140

ATT GTT GTC ATG ACT ATC CTC CTG GTG GTT CTG TAT AAA TAC AGG TGC    722
Ile Val Val Met Thr Ile Leu Leu Val Val Leu Tyr Lys Tyr Arg Cys
            145                     150                     155

TAT AAG GTC ATC CAT GCC TGG CTT ATT ATA TCA TCT CTA TTG TTG CTG    770
Tyr Lys Val Ile His Ala Trp Leu Ile Ile Ser Ser Leu Leu Leu Leu
            160                     165                     170
```

FIG. 4E

```
TTC TTT TTT TCA TTC ATT TAC TTG GGG GAA GTG TTT AAA ACC TAT AAC    818
Phe Phe Phe Ser Phe Ile Tyr Leu Gly Glu Val Phe Lys Thr Tyr Asn
175                     180                     185                 190

GTT GCT GTG GAC TAC ATT ACT GTT GCA CTC CTG ATC TGG AAT TTT GGT    866
Val Ala Val Asp Tyr Ile Thr Val Ala Leu Leu Ile Trp Asn Phe Gly
                195                     200                     205

GTG GTG GGA ATG ATT TCC ATT CAC TGG AAA GGT CCA CTT CGA CTC CAG    914
Val Val Gly Met Ile Ser Ile His Trp Lys Gly Pro Leu Arg Leu Gln
        210                     215                     220

CAG GCA TAT CTC ATT ATG AGT GCC CTC ATG GCC CTG GTG TTT ATC        962
Gln Ala Tyr Leu Ile Met Ile Ser Ala Leu Met Ala Leu Val Phe Ile
225                     230                     235
```

FIG. 4F

```
AAG TAC CTC CCT GAA TGG ACT GCG TGG CTC ATC TTG GCT GTG ATT TCA    1010
Lys Tyr Leu Pro Glu Trp Thr Ala Trp Leu Ile Leu Ala Val Ile Ser
 240                         245                         250

GTA TAT GAT TTA GTG GCT GTT TTG TGT CCG AAA GGT CCA CTT CGT ATG    1058
Val Tyr Asp Leu Val Ala Val Leu Cys Pro Lys Gly Pro Leu Arg Met
 255                         260                         265                  270

CTG GTT GAA ACA GCT CAG GAG AGA AAT GAA ACG CTT TTT CCA GCT CTC    1106
Leu Val Glu Thr Ala Gln Glu Arg Asn Glu Thr Leu Phe Pro Ala Leu
                             275                         280                  285

ATT TAC TCC TCA ACA ATG GTG TGG TTG GTG AAT ATG GCA GAA GGA GAC    1154
Ile Tyr Ser Ser Thr Met Val Trp Leu Val Asn Met Ala Glu Gly Asp
             290                         295                         300
```

FIG. 4G

```
CCG GAA GCT CAA AGG AGA GTA TCC AAA AAT TCC AAG TAT AAT GCA GAA    1202
Pro Glu Ala Gln Arg Arg Val Ser Lys Asn Ser Lys Tyr Asn Ala Glu
        305                 310                 315

AGC ACA GAA AGG GAG TCA CAA GAC ACT GTT GCA GAG AAT GAT GAT GGC    1250
Ser Thr Glu Arg Glu Ser Gln Asp Thr Val Ala Glu Asn Asp Asp Gly
        320                 325                 330

GGG TTC AGT GAG GAA TGG GAA GCC CAG AGG GAC AGT CAT CTA GGG CCT    1298
Gly Phe Ser Glu Glu Trp Glu Ala Gln Arg Asp Ser His Leu Gly Pro
335                 340                 345                 350

CAT CGC TCT ACA CCT GAG TCA CGA GCT GCT GTC CAG GAA CTT TCC AGC    1346
His Arg Ser Thr Pro Glu Ser Arg Ala Ala Val Gln Glu Leu Ser Ser
        355                 360                 365
```

FIG. 4H

```
AGT ATC CTC GCT GGT GAA GAC CCA GAG GAA AGG GGA GTA AAA CTT GGA    1394
Ser Ile Leu Ala Gly Glu Asp Pro Glu Glu Arg Gly Val Lys Leu Gly
370                          375                        380

TTG GGA GAT TTC ATT TTC TAC AGT GTT CTG GTT GGT AAA GCC TCA GCA    1442
Leu Gly Asp Phe Ile Phe Tyr Ser Val Leu Val Gly Lys Ala Ser Ala
        385                          390                       395

ACA GCC AGT GGA GAC TGG AAC ACA ACC ATA GCC TGT TTC GTA GCC ATA    1490
Thr Ala Ser Gly Asp Trp Asn Thr Thr Ile Ala Cys Phe Val Ala Ile
400                          405                        410

TTA ATT GGT TTG TGC CTT ACA TTA CTC CTT GCC ATT TTC AAG AAA        1538
Leu Ile Gly Leu Cys Leu Thr Leu Leu Leu Ala Ile Phe Lys Lys
415                     420                      425           430
```

FIG. 4I

```
GCA TTG CCA GCT CTT CCA ATC TCC ATC ACC TTT GGG CTT GTT TTC TAC    1586
Ala Leu Pro Ala Leu Pro Ile Ser Ile Thr Phe Gly Leu Val Phe Tyr
            435                 440                 445

TTT GCC ACA GAT TAT CTT GTA CAG CCT TTT ATG GAC CAA TTA GCA TTC    1634
Phe Ala Thr Asp Tyr Leu Val Gln Pro Phe Met Asp Gln Leu Ala Phe
            450                 455                 460

CAT CAA TTT TAT ATC TAG CATATATTGCG GTTAGAATCC CATGGATGTT          1682
His Gln Phe Tyr Ile
        465

TCTTCTTTGA CTATAACCAA ATCTGGGGAG GACAAAGGTG ATTTTCCTGT GTCCACATCT  1742

AACAAAGTCA AGATTCCCGG CTGGACTTTT GCAGCTTCCT TCCAAGTCTT CCTGACCACC  1802

TTGCACTATT GGACTTTGGA AGGAGGTGCC TATAGAAAAC GATTTTGAAC ATACTTCATC  1862
```

FIG. 4J

```
GCAGTGGACT GTGTCCCTCG GTGCAGAAAC TACCAGATTT GAGGGACGAG GTCAAGGAGA  1922

TATGATAGGC CCGGAAGTTG CTGTGCCCCA TCAGCAGCTT GACGCGTGGT CACAGGACGA  1982

TTTCACTGAC ACTGCGAACT CTCAGGACTA CCGGTTACCA AGAGGTTAGG TGAAGTGGTT  2042

TAAACCAAAC GGAACTCTTC ATCTTAAACT ACACGTTGAA AATCAACCCA ATAATTCTGT  2102

ATTAACTGAA TTCTGAACTT TTCAGGAGGT ACTGTGAGGA AGAGCAGGCA CCAGCAGCAG  2162

AATGGGGAAT GGAGAGGTGG GCAGGGGTTC CAGCTTCCCT TTGATTTTTT GCTGCAGACT  2222

CATCCTTTTT AAATGAGACT TGTTTCCCC TCTCTTTGAG TCAAGTCAAA TATGTAGATT  2282

GCCTTGGCA ATTCTTCTTC TCAAGCACTG ACACTCATTA CCGTCTGTGA TTGCCATTTC  2342
```

FIG. 4K

```
TTCCCAAGGC CAGTCTGAAC CTGAGGTTGC TTTATCCTAA AAGTTTTAAC CTCAGGTTCC    2402

AAATTCAGTA AATTTTGGAA ACAGTACAGC TATTTCTCAT CAATTCTCTA TCATGTTGAA    2462

GTCAAATTTG GATTTTCCAC CAAATTCTGA ATTTGTAGAC ATACTTGTAC GCTCACTTGC    2522

CCCCAGATGC CTCCTCTGTC TCATTCTTC  TCTCCCACAC AAGCAGTCTT TTTCTACAGC    2582

CAGTAAGGCA GCTCTGTCTG GTAGCAGATG GTCCCATTAT TCTAGGGTCT TACTCTTTGT    2642

ATGATGAAAA GAATGTGTTA TGAATCGGTG CTGTCAGCCC TGCTGTCAGA CCTTCTTCCA    2702

CAGCAAATGA GATGTATGCC CAAAGCGGTA GAATTAAAGA AGAGTAAAAT GGCTGTTGAA    2762

GC                                                                  2764
```

FIG. 4L (2) INFORMATION FOR SEQ ID NO: 3:

(i) SEQUENCE CHARACTERISTICS:

(A) LENGTH: 468 amino acids (B) TYPE: amino acid (D) TOPOLOGY: linear

FIG. 5B (ii) MOLECULE TYPE: protein (xi) SEQUENCE DESCRIPTION: SEQ ID NO: 3:

```
Met Thr Glu Leu Pro Ala Pro Leu Ser Tyr Phe Gln Asn Ala Gln Met
 1               5                  10                  15
Ser Glu Asp Asn His Leu Ser Asn Thr Val Arg Ser Gln Asn Asp Asn
                20                  25                  30
Arg Glu Arg Gln Glu His Asn Asp Arg Arg Ser Leu Gly His Pro Glu
                35                  40                  45
Pro Leu Ser Asn Gly Arg Pro Gln Gly Asn Ser Arg Gln Val Val Glu
                50                  55                  60
```

```
Gln Asp Glu Glu Glu Asp Glu Glu Leu Thr Leu Lys Tyr Gly Ala Lys
 65                  70                  75                  80

His Val Ile Met Leu Phe Val Pro Val Thr Leu Cys Met Val Val Val
                     85                  90                  95

Val Ala Thr Ile Lys Ser Val Ser Phe Tyr Thr Arg Lys Asp Gly Gln
                    100                 105                 110

Leu Ile Tyr Thr Pro Phe Thr Glu Asp Thr Glu Thr Val Gly Gln Arg
                    115                 120                 125

Ala Leu His Ser Ile Leu Asn Ala Ala Ile Met Ile Ser Val Ile Val
                    130                 135                 140
```

FIG. 5C

```
Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
                195                 200                 205

Gly Met Ile Ser Ile His Trp Lys Gly Pro Leu Arg Leu Gln Gln Ala
210                 215                 220
```

FIG. 5D

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
            245                 250                 255

Asp Leu Val Ala Val Leu Cys Pro Lys Gly Pro Leu Arg Met Leu Val
        260                 265                 270

Glu Thr Ala Gln Glu Arg Asn Glu Thr Leu Phe Pro Ala Leu Ile Tyr
    275                 280                 285

Ser Ser Thr Met Val Trp Leu Val Asn Met Ala Glu Gly Asp Pro Glu
290                 295                 300

FIG. 5E (2) INFORMATION FOR SEQ ID NO: 4:

(i) SEQUENCE CHARACTERISTICS:

(A) LENGTH: 3148 base pairs (B) TYPE: nucleic acid (C) STRANDEDNESS: single (D) TOPOLOGY: linear

FIG. 6A

FIG. 6B (ii) MOLECULE TYPE: cDNA to mRNA (iv) ANTI-SENSE: NO (ix) FEATURE:
 (A) NAME/KEY: CDS
 (B) LOCATION:125..2380

(xi) SEQUENCE DESCRIPTION: SEQ ID NO: 4:

GAATTCCCGC GGAGCAGCGT GCGCGGGGCC CCGGGAGACG GCGGCGGGTAG CGGCGCGGGC    60

AGAGCAAGGA CGCGGGCGGAT CCCACTCGCA CAGCAGCGCA CTCGGTGCCC CGGCAGGGT   120

```
CGCG ATG CTG CCC GGT TTG GCA CTG CTC CTG CTG GCC GCC TGG ACG GCT    169
     Met Leu Pro Gly Leu Ala Leu Leu Leu Leu Ala Ala Trp Thr Ala
     470                 475                 480

CGG GCG CTG GAG GTA CCC ACT GAT GGT AAT GCT GGC CTG CTG GCT GAA    217
Arg Ala Leu Glu Val Pro Thr Asp Gly Asn Ala Gly Leu Leu Ala Glu
485                 490                 495

CCC CAG ATT GCC ATG TTC TGT GGC AGA CTG AAC ATG CAC ATG AAT GTC    265
Pro Gln Ile Ala Met Phe Cys Gly Arg Leu Asn Met His Met Asn Val
500                 505                 510                 515

TAC TGC ATG GCC GTG TGT GGC AGC GCC ATT CCT ACA ACA GCA GCC AGT   1177
Tyr Cys Met Ala Val Cys Gly Ser Ala Ile Pro Thr Thr Ala Ala Ser
805                 810                 815
```

FIG. 6C

```
ACC CCT GAT GCC GTT GAC AAG TAT CTC GAG ACA CCT GGG GAT GAG AAT    1225
Thr Pro Asp Ala Val Asp Lys Tyr Leu Glu Thr Pro Gly Asp Glu Asn
820                 825                 830                 835

GAA CAT GCC CAT TTC CAG AAA GCC AAA GAG AGG CTT GAG GCC AAG CAC    1273
Glu His Ala His Phe Gln Lys Ala Lys Glu Arg Leu Glu Ala Lys His
            840                 845                 850

CGA GAG AGA ATG TCC CAG GTC ATG AGA GAA TGG GAA GAG GCA GAA CGT    1321
Arg Glu Arg Met Ser Gln Val Met Arg Glu Trp Glu Glu Ala Glu Arg
        855                 860                 865

CAA GCA AAG AAC TTG CCT AAA GCT GAT AAG AAG GCA GTT ATC CAG CAT    1369
Gln Ala Lys Asn Leu Pro Lys Ala Asp Lys Lys Ala Val Ile Gln His
    870                 875                 880
```

FIG. 6D

```
TTC CAG GAG AAA GTG GAA TCT TTG GAA CAG GAA GCA GCC AAC GAG AGA         1417
Phe Gln Glu Lys Val Glu Ser Leu Glu Gln Glu Ala Ala Asn Glu Arg
            885                 890                 895

CAG CAG CTG GTG GAG ACA CAC ATG GCC AGA GTG GAA GCC ATG CTC AAT         1465
Gln Gln Leu Val Glu Thr His Met Ala Arg Val Glu Ala Met Leu Asn
        900                 905                 910             915

GAC CGC CGC CGC CTG GCC CTG GAG AAC TAC ATC ACC GCT CTG CAG GCT         1513
Asp Arg Arg Arg Leu Ala Leu Glu Asn Tyr Ile Thr Ala Leu Gln Ala
                920                 925                 930

GTT CCT CCT CGG CCT CGT CAC GTG TTC AAT ATG CTA AAG AAG TAT GTC         1561
Val Pro Pro Arg Pro Arg His Val Phe Asn Met Leu Lys Lys Tyr Val
            935                 940                 945
```

FIG. 6E

```
CGC GCA GAA CAG AAG GAC AGA CAG CAC ACC CTA AAG CAT TTC GAG CAT    1609
Arg Ala Glu Gln Lys Asp Arg Gln His Thr Leu Lys His Phe Glu His
            950                     955                     960

GTG CGC ATG GTG GAT CCC AAG AAA GCC GCT CAG ATC CGG TCC CAG GTT    1657
Val Arg Met Val Asp Pro Lys Lys Ala Ala Gln Ile Arg Ser Gln Val
        965                     970                     975

ATG ACA CAC CTC CGT GTG ATT TAT GAG CGC ATG AAT CAG TCT CTC TCC    1705
Met Thr His Leu Arg Val Ile Tyr Glu Arg Met Asn Gln Ser Leu Ser
    980                     985                     990         995

CTG CTC TAC AAC GTG CCT GCA GTG GCC GAG GAG ATT CAG GAT GAA GTT    1753
Leu Leu Tyr Asn Val Pro Ala Val Ala Glu Glu Ile Gln Asp Glu Val
                1000                    1005                    1010
```

FIG. 6F

```
GAC TCT GTG CCA GCC AAC ACA GAA AAC GAA GTT GAG CCT GTT GAT GCC       1993
Asp Ser Val Pro Ala Asn Thr Glu Asn Glu Val Glu Pro Val Asp Ala
                1080                    1085                 1090

CGC CCT GCT GCC GAC CGA GGA CTG ACC ACT CGA CCA GGT TCT GGG TTG       2041
Arg Pro Ala Ala Asp Arg Gly Leu Thr Thr Arg Pro Gly Ser Gly Leu
                1095                    1100                1105

ACA AAT ATC AAG ACG GAG GAG ATC TCT GAA GTG AAG ATG GAT GCA GAA       2089
Thr Asn Ile Lys Thr Glu Glu Ile Ser Glu Val Lys Met Asp Ala Glu
                1110                    1115                1120

TTC CGA CAT GAC TCA GGA TAT GAA GTT CAT CAT CAA AAA TTG GTG TTC       2137
Phe Arg His Asp Ser Gly Tyr Glu Val His His Gln Lys Leu Val Phe
                1125                    1130                1135
```

FIG. 6G

```
GAC TCT GTG CCA GCC AAC ACA GAA AAC GAA GTT GAG CCT GTT GAT GCC      1993
Asp Ser Val Pro Ala Asn Thr Glu Asn Glu Val Glu Pro Val Asp Ala
                1080                1085                1090

CGC CCT GCT GCC GAC CGA GGA CTG ACC ACT CGA CCA GGT TCT GGG TTG      2041
Arg Pro Ala Ala Asp Arg Gly Leu Thr Thr Arg Pro Gly Ser Gly Leu
                1095                1100                1105

ACA AAT ATC AAG ACG GAG GAG ATC TCT GAA GTG AAG ATG GAT GCA GAA      2089
Thr Asn Ile Lys Thr Glu Glu Ile Ser Glu Val Lys Met Asp Ala Glu
                1110                1115                1120

TTC CGA CAT GAC TCA GGA TAT GAA GTT CAT CAT CAA AAA TTG GTG TTC      2137
Phe Arg His Asp Ser Gly Tyr Glu Val His His Gln Lys Leu Val Phe
                1125                1130                1135
```

FIG. 6H

```
TTT GCA GAA GAT GTG GGT TCA AAC AAA GGT GCA ATC ATT GGA CTC ATG    2185
Phe Ala Glu Asp Val Gly Ser Asn Lys Gly Ala Ile Ile Gly Leu Met
            1140                1145                1150                1155

GTG GGC GGT GTT GTC ATA GCG ACA GTG ATC GTC ATC ACC TTG GTG ATG    2233
Val Gly Gly Val Val Ile Ala Thr Val Ile Val Ile Thr Leu Val Met
            1160                1165                1170

CTG AAG AAA CAG TAC ACA TCC ATT CAT CAT GGT GTG GTG GAG GTT        2281
Leu Lys Lys Gln Tyr Thr Ser Ile His His Gly Val Val Glu Val
        1175                1180                1185

GAC GCC GCT GTC ACC CCA GAG GAG CGC CAC CTG TCC AAG ATG CAG CAG    2329
Asp Ala Ala Val Thr Pro Glu Glu Arg His Leu Ser Lys Met Gln Gln
            1190                1195                1200
```

FIG. 61

```
AAC GGC TAC GAA AAT CCA ACC TAC AAG TTC TTT GAG CAG ATG CAG AAC     2377
Asn Gly Tyr Glu Asn Pro Thr Tyr Lys Phe Phe Glu Gln Met Gln Asn
        1205                    1210                    1215

TAG ACCCCCGCCA CAGCAGCCTC TGAAGTTGGA CAGCAAAACC ATTGCTTCAC           2430
 *
1220

TACCCATCGG TGTCCATTTA TAGAATAATG TGGGAAGAAA CAAACCCGTT TTATGATTTA    2490

CTCATTATCG CCTTTTGACA GCTGTGCTGT AACACAAGTA GATGCCTGAA CTTGAATTAA    2550

TCCACACATC AGTAATGTAT TCTATCTCTC TTTACATTTT GGTCTCTATA CTACATTATT    2610

AATGGGTTTT GTGTACTGTA AAGAATTTAG CTGTATCAAA CTAGTGCATG AATAGATTCT    2670
```

FIG. 6J

```
CTCCTGATTA TTTATCACAT AGCCCCTTAG CCAGTTGTAT ATTATTCTTG TGGTTTGTGA    2730

CCCAATTAAG TCCTACTTTA CATATGCTTT AAGAATCGAT GGGGGATGCT TCATGTGAAC    2790

GTGGGAGTTC AGCTGCTTCT CTTGCCTAAG TATTCCTTTC CTGATCACTA TGCATTTTAA    2850

AGTTAAACAT TTTAAGTAT TTCAGATGCT TTAGAGAGAT TTTTTTTCCA TGACTGCATT    2910

TTACTGTACA GATTGCTGCT TCTGCTATAT TTGTGATATA GGAATTAAGA GGATACACAC    2970

GTTTGTTTCT TCGTGCCTGT TTTATGTGCA CACATTAGGC ATTGAGACTT CAAGCTTTTC    3030

TTTTTTTGTC CACGTATCTT TGGGTCTTTG ATAAAGAAAA GAATCCCTGT TCATTGTAAG    3090

CACTTTTACG GGGCGGGTGG GGAGGGGTGC TCTGCTGGTC TTCAATTACC AAGAATTC     3148
```

FIG. 6K

FIG. 7A (2) INFORMATION FOR SEQ ID NO: 5:

(i) SEQUENCE CHARACTERISTICS:

(A) LENGTH: 752 amino acids
(B) TYPE: amino acid
(D) TOPOLOGY: linear (ii) MOLECULE TYPE: protein (xi) SEQUENCE DESCRIPTION: SEQ ID NO: 5:

```
Met Leu Pro Gly Leu Ala Leu Leu Leu Leu Ala Ala Trp Thr Ala Arg
 1               5                  10                  15
Ala Leu Glu Val Pro Thr Asp Gly Asn Ala Gly Leu Leu Ala Glu Pro
            20                  25                  30
```

Gln Ile Ala Met Phe Cys Gly Arg Leu Asn Met His Met Asn Val Gln
             35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
             100                 105                 110

FIG. 7B

Ile Pro Tyr Arg Cys Leu Val Gly Glu Phe Val Ser Asp Ala Leu Leu
115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
165                 170                 175

Asp Lys Phe Arg Gly Val Glu Phe Val Cys Cys Pro Leu Ala Glu Glu
180                 185                 190

FIG. 7C

```
Ser Asp Asn Val Asp Ser Ala Asp Ala Glu Glu Asp Ala Asp Ser Asp Val
            195                 200                 205

Trp Trp Gly Gly Ala Asp Thr Asp Tyr Ala Asp Gly Ser Glu Asp Lys
        210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Glu Pro Tyr Glu Glu Ala Thr Glu Arg Thr Thr Ser Ile
            260                 265                 270
```

FIG. 7D

Ala Thr Thr Thr Thr Thr Glu Ser Val Glu Glu Val Val Arg
275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
325                 330                 335

Cys Met Ala Val Cys Gly Ser Ala Ile Pro Thr Thr Ala Ala Ser Thr
340                 345                 350

FIG. 7E

Pro Asp Ala Val Asp Lys Tyr Leu Glu Thr Pro Gly Asp Glu Asn Glu
355                                 360                                 365

His Ala His Phe Gln Lys Ala Lys Glu Arg Leu Glu Ala Lys His Arg
370                                 375                                 380

Glu Arg Met Ser Gln Val Met Arg Glu Trp Glu Glu Ala Glu Arg Gln
385                                 390                                 395                                 400

Ala Lys Asn Leu Pro Lys Ala Asp Lys Lys Ala Val Ile Gln His Phe
405                                 410                                 415

Gln Glu Lys Val Glu Ser Leu Glu Gln Glu Ala Ala Asn Glu Arg Gln
420                                 425                                 430

FIG. 7F

Gln Leu Val Glu Thr His Met Ala Arg Val Glu Ala Met Leu Asn Asp
435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
485                 490                 495

Arg Met Val Asp Pro Lys Lys Ala Ala Gln Ile Arg Ser Gln Val Met
500                 505                 510

FIG. 7G

Thr His Leu Arg Val Ile Tyr Glu Arg Met Asn Gln Ser Leu Ser Leu
515                 520                 525

Leu Tyr Asn Val Pro Ala Val Ala Glu Glu Ile Gln Asp Glu Val Asp
530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
565                 570                 575

Ser Leu Thr Glu Thr Lys Thr Thr Val Glu Leu Leu Pro Val Asn Gly
580                 585                 590

FIG. 7H

Glu Phe Ser Leu Asp Asp Leu Gln Pro Trp His Ser Phe Gly Ala Asp
595                 600                 605

Ser Val Pro Ala Asn Thr Glu Asn Glu Val Glu Pro Val Asp Ala Arg
610                 615                 620

Pro Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
645                 650                 655

Arg His Asp Ser Gly Tyr Glu Val His His Gln Lys Leu Val Phe Phe
660                 665                 670

FIG. 71

Ala Glu Asp Val Gly Ser Asn Lys Gly Ala Ile Ile Gly Leu Met Val
675                 680                 685

Gly Gly Val Val Ile Ala Thr Val Ile Val Ile Thr Leu Val Met Leu
        690                 695                 700

Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
            725                 730                 735

Gly Tyr Glu Asn Pro Thr Tyr Lys Phe Phe Glu Gln Met Gln Asn *
    740                 745                 750

FIG. 7J (2) INFORMATION FOR SEQ ID NO: 6:

(i) SEQUENCE CHARACTERISTICS:

(A) LENGTH: 20 base pairs (B) TYPE: nucleic acid (C) STRANDEDNESS: single (D) TOPOLOGY: linear (ii) MOLECULE TYPE: other nucleic acid (iv) ANTI-SENSE: NO (xi) SEQUENCE DESCRIPTION: SEQ ID NO: 6:

AATCGGATCC ATGGCTTCAC          20

(2) INFORMATION FOR SEQ ID NO: 7:

(i) SEQUENCE CHARACTERISTICS:

(A) LENGTH: 23 base pairs
      (B) TYPE: nucleic acid
      (C) STRANDEDNESS: single
      (D) TOPOLOGY: linear (ii) MOLECULE TYPE: other nucleic acid (iv) ANTI-SENSE: NO (xi) SEQUENCE DESCRIPTION: SEQ ID NO: 7:

CCGAATTCTG TCCGAAAGGT CCA   23

(2) INFORMATION FOR SEQ ID NO: 8:

(i) SEQUENCE CHARACTERISTICS:

(A) LENGTH: 26 base pairs (B) TYPE: nucleic acid (C) STRANDEDNESS: single (D) TOPOLOGY: linear (ii) MOLECULE TYPE: DNA (genomic)

(iv) ANTI-SENSE: NO (xi) SEQUENCE DESCRIPTION: SEQ ID NO: 8:

CCGGATCCCT AGGTTGTGTT CCAGTC

DNA MOLECULES COMPRISING A PROMOTER CAPABLE OF CONFERRING EXPRESSION OF A HETEROLOGOUS DNA SEQUENCE

Reference is made to the concurrently-filed application of Ralf Baumeister, Ser. No. 08/832643, now abandoned, which is incorporated herein by reference.

FIELD OF THE INVENTION

The present invention relates to recombinant DNA molecules comprising the promoter region of the sel-12 gene of *Caenorhabditis elegans* (*C. elegans*) or promoter regions of genes homologous to the sel-12 gene, being capable of conferring expression of a heterologous DNA sequence in neural cells, advantageously all neural cells, preferably at all stages of development. The present invention also provides vectors comprising the DNA molecules. The present invention also relates to pharmaceutical and diagnostic compositions comprising such recombinant DNA molecules and vectors. Furthermore, the present invention relates to transgenic animals, e.g., in species ranging from the fruit fly to mammals, such as non-human animals, comprising the aforementioned recombinant DNA molecules or vectors stably integrated into their genome, as well as their use for the identification of substances capable of complementing a neuronal disorder. The present invention also relates to the use of the inventive recombinant DNA molecules and vectors for the preparation of pharmaceutical compositions for treating, preventing, and/or delaying a neuronal disorder in a subject. Furthermore, the recombinant DNA molecules and vectors of the invention also can be used for the preparation of pharmaceutical compositions for inducing a neuronal disorder in a non-human animal.

Several documents are cited throughout the text of this specification with a References section provided prior to the claims. Citations can be in the form of a numerical designation or designations in brackets, with the numerical designation or designations corresponding to a document or documents similarly numbered in the Reference section. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

In the field of neuroscience and medical therapy, there is a great demand for test systems to study the function and interaction of gene products, the malfunction or expression of which cause neuronal diseases. Such systems would also be suitable for drug development against neuronal diseases. A prominent example for a neuronal disease is familial Alzheimer's disease (FAD). The majority of cases with FAD are linked to mutations of the presenilin (PS) genes. These genes are homologous to the sel-12 gene of *C. elegans*, which has been postulated to function in the facilitated signaling by lin-12 and glp-1 [15].

Of the genes involved in FAD, mutations within the PS genes are most frequently associated with the early onset of the disease [1]. These genes encode two highly homologous proteins (PS-1, PS-2) [1-5] which appear to adopt a seven to nine transmembrane (TM) domain structure [1-5]. Most of the mutations which co-segregate with FAD patients occur within the PS-1 gene whereas only two mutations have been identified within the PS-2 gene so far [1-5]. Both PS proteins are predominantly located within the endoplasmic reticulum and the early Golgi [6-8], where they co-localize with the β-amyloid precursor protein (βAPP) [7]. Mutations in the PS genes cause elevated levels of the long form of amyloid β-peptide terminating at amino acid 42/43 [5, 9, 10], the key player in sporadic Alzheimer's disease (AD) as well as in FAD [11]. It was shown recently that PS-1 is proteolytically cleaved [12, 13] within the large loop between TM6 and TM7[13]. Since endogenous full-length PS proteins were not detected [7, 12, 13], it was suggested that the proteolytic fragments of PS proteins exhibit their biological function. This is further supported by the finding that the FAD associates PS-1 Δexon9 mutant [14] which lacks the cleavage site, accumulated as full-length protein [12].

The biological functions of the PS proteins are yet unknown. However, sequence similarities to the *C. elegans* sel-12 [15] (42%) and to a lesser extent to the SPC-4 [1, 16] proteins suggest a functional conservation of these proteins. The conservation of topology of sel-12 and PS-1 further supports this assumption [17, 18]. Interestingly, the FAD linked mutations within the human PS genes all occur at positions which are conserved with the two homologous *C. elegans* genes [1-5, 15, 16] suggesting that these mutations are located at functionally important positions. Mutations in sel-12 suppress the Multivulva phenotype of an hyper-active lin-12/Notch mutant. sel-12 mutants themselves have a strong egg-laying (Egl) defect which is reminiscent of the Egl phenotype caused by reducing lin-12 activity [15]. These results suggested that sel-12 is either directly involved in lin-12 signaling or in the receptor transport or recycling [15].

Recently, Levitan [20] developed a model system to study PS structure and function in *C. elegans*. In their system, PS-1 was expressed from an engineered lin-12 promoter variant described in Wilkinson and Greenwald [23]. This promoter is expressed in the vulva precursor cells, most likely the only cells where sel-12 function is required for the correct execution of egg-laying behavior. It was shown that PS-1 expression in the vulva precursor cells can functionally replace sel-12. For studying all aspects of genes involved in neuronal diseases such as FAD, in particular their effect on the psycho/motoric system however, the system described by Levitan [20] suffers from several drawbacks.

For example, although the PS genes in humans are ubiquitously expressed [2, 3], their neural expression is a prerequisite for understanding their role in the pathophysiology of FAD [6]. The promoter employed in Levitan [20], however, is not expressed in most neural cells, and, therefore, defects of sel-12 mutants like an uncoordinated (kinker) phenotype and a general lethargy of the animals cannot be complemented by their promoter constructs. Furthermore, the lin-12 promoter only functions efficiently in the genetic background of smg-1 mutants [23]. However, smg-1 mutants significantly suppress the sel-12 phenotype [20].

Thus, a technical problem present in the art and believed not heretofore provided is providing promoter regions capable of conferring expression of a heterologous DNA sequence in all neural cells, preferably at all stages of development.

OBJECTS AND SUMMARY OF THE INVENTION

Since Alzheimer is a disease of the nervous system, the inventor decided to study the function and interaction of proteins involved in this disease in neural cells since otherwise non-informative or even false positive results may be obtained.

Thus, an object of the present invention can be to provide promoter regions capable of conferring the expression of a heterologous DNA sequence in neural cells, advantageously all neural cells, and preferably at all stages of development. Accordingly, it is an object of the invention to address, and preferably provide a solution, to the technical problem in the art, by providing embodiments of the invention.

Further objects of the invention can include providing, inter alia:

an isolated nucleic acid molecule, e.g., a nucleotide sequence such as an isolated DNA molecule or a recombinant DNA molecule comprising the promoter of the sel-12 gene from C. elegans or the promoter region of a gene homologous to the sel-12 gene being-capable of conferring expression in neural cells, advantageously all neural cells, and preferably at all stages of development, and optionally operatively linked thereto at least one isolated nucleic acid molecule or nucleotide-sequence, e.g., a heterologous DNA sequence;

a vector comprising at least one inventive isolated nucleic acid molecule, e.g., recombinant DNA molecule;

a pharmaceutical composition comprising at least one inventive isolated nucleic acid molecule, e.g., recombinant DNA molecule and/or vector, and optionally a pharmaceutically acceptable carrier;

a diagnostic composition comprising at least one inventive isolated nucleic acid molecule, e.g., recombinant DNA molecule and/or vector, and optionally suitable means for detection;

a transgenic non-human animal comprising stably integrated into its genome at least one inventive isolated nucleic acid molecule, e.g., recombinant DNA molecule and/or vector;

a method for the identification of a chemical and/or biological substance capable of complementing a neuronal disorder comprising contacting an inventive transgenic non-human animal (preferably having a neuronal disorder, such as from containing at least one inventive isolated nucleic acid molecule) with a plurality of compounds, and determining those compounds which are capable of complementing the neuronal disorder of the transgenic non-human animal;

a method for the identification of a chemical and/or biological substance capable of interfering Presenilin/APP interaction comprising: contacting an inventive transgenic non-human animal (preferably having Presenilin/APP interaction, such as from containing at least one inventive isolated nucleic acid molecule) with a plurality of compounds, and determining those compounds which are capable of interfering with Presenilin/APP interaction; and use of at least one inventive transgenic non-human animal for identifying a substance capable of complementing a neuronal disorder or a method for identifying a substance capable of complementing a neuronal disorder (the use or method can comprise administering a substance to an inventive transgenic non-human animal and determining whether the substance complements the physical and/or behavioral disorder displayed by the transgenic non-human animal as a result of a mutant sel-12 gene or gene which is homologous to the sel-12 gene).

Accordingly, the present invention provides an isolated nucleic acid molecule, e.g., an isolated or recombinant DNA molecule, comprising:

(a) the promoter region of the sel-12 gene from C. elegans or a promoter region of a gene homologous to the-sel-12 gene being capable of conferring expression in neural cells, advantageously substantially all neural cells, preferably at substantially all stages of development; and optionally (b) operatively linked thereto at least one heterologous nucleic acid molecule, e.g., an isolated nucleic acid molecule such as DNA, for instance such a nucleic acid molecule comprising a coding sequence.

Further embodiments of the invention can include, inter alia:

an isolated nucleic acid molecule, e.g., a nucleotide sequence such as an isolated DNA molecule or a recombinant DNA molecule comprising the promoter of the sel-12 gene from C. elegans or the promoter region of a gene homologous to the sel-12 gene being capable of conferring expression in neural cells, advantageously all neural cells, and preferably at all stages of development, and operatively linked thereto at least one isolated nucleic acid molecule or nucleotide sequence, e.g., a heterologous DNA sequence;

a vector comprising at least one inventive isolated nucleic acid molecule$_6$ e.g., recombinant DNA molecule;

a pharmaceutical composition comprising at least one inventive isolated nucleic acid molecule, e.g., recombinant DNA molecule and/or vector, and optionally a pharmaceutically acceptable carrier;

a diagnostic composition comprising at least one inventive isolated nucleic acid molecule, e.g., recombinant DNA molecule and/or vector, and optionally suitable means for detection;

a transgenic non-human animal comprising stably integrated into its genome at least one inventive isolated nucleic acid molecule, e.g., recombinant DNA molecule and/or vector;

a method for the identification of a chemical and/or biological substance capable of complementing a neuronal disorder comprising contacting an inventive transgenic non-human animal (preferably having a neuronal disorder, such as from containing at least one inventive isolated nucleic acid molecule) with a plurality of compounds, and determining those compounds which are capable of complementing the neuronal disorder of the transgenic non-human animal;

a method for the identification of a chemical and/or biological substance capable of interfering Presenilin/APP interaction comprising: contacting an inventive transgenic non-human animal (preferably having Presenilin/APP interaction, such as from containing at least one inventive isolated nucleic acid molecule) with a plurality of compounds, and determining those compounds which are capable of interfering with Presenilin/APP interaction; and use of at least one inventive transgenic non-human animal for identifying a substance capable of complementing a neuronal disorder or a method for identifying a substance capable of complementing a neuronal disorder (the use or method can comprise administering a substance to an inventive transgenic non-human animal and determining whether the substance complements the physical and/or behavioral disorder displayed by the transgenic non-human animal as a result of a mutant sel-12 gene or gene which is homologous to the sel-12 gene).

The promoter region can comprises the nucleotide sequence as depicted in SEQ ID NO: 1 (FIG. 3) part(s)

thereof which capable of conferring expression in all neural cells at all stages of development.

The exogenous or heterologous DNA sequence can encode a protein or functional part thereof involved in neuronal development and/or diseases, for instance a protein involved in Alzheimer disease, e.g., Presenilin or a functional part thereof, or a protein which is functionally equivalent to Presenilin or a part thereof. The protein can be encoded by a DNA sequence selected from the group consisting of (a) DNA sequences comprising a nucleotide sequence encoding the sequence as given in SEQ ID NO: 3 (FIG. 5);

(b) DNA sequences comprising the nucleotide sequence as given in SEQ ID NO: 2 (FIG. 4);

(c) DNA sequences comprising a nucleotide sequence which hybridizes with a complementary strand of a nucleotide sequence of (a) or (b); and (d) DNA sequences comprising a nucleotide sequence which is degenerate to a nucleotide sequence of (c).

The exogenous or heterologous DNA sequence can encode the amyloid precursor protein (APP) or its proteolytic product (Aβ), a functional part thereof or a protein functional equivalent to APP or Aβ or any mutated versions thereof. The exogenous or heterologous DNA sequence can be selected from the group consisting of DNA sequences comprising a nucleotide sequence encoding the amino acid sequence as given in SEQ ID NO: 5 (FIG. 7);

(b) DNA sequences comprising the nucleotide sequence as given in SEQ ID NO: 4 (FIG. 6);

(c) DNA sequences comprising a nucleotide sequence which hybridizes with a complementary strand of a nucleotide sequence of (a) or (b); and (d) DNA sequences comprising a nucleotide sequence which is degenerate to a nucleotide sequence of (c).

The exogenous or heterologous DNA sequence can encode a mutated version of a protein which has lost its capability of complementation of a sel-12 mutant phenotype.

The vector can include one or more of the inventive isolated nucleic acid molecules, e.g., recombinant DNA molecules, or one or more exogenous or heterologous isolated nucleic acid molecules, e.g., exogenous or heterologous DNA sequences.

For instance, an inventive vector can contain at least one exogenous or heterologous DNA sequence encoding: (i) a protein or functional part thereof involved in neuronal development and/or diseases, for instance a protein involved in Alzheimer disease, e.g., Presenilin or a functional part thereof, or a protein which is functionally equivalent to Presenilin or a part thereof, for instance, the protein can be encoded by a DNA sequence selected from the group consisting of (a) DNA sequences comprising a nucleotide sequence encoding the sequence as given in SEQ ID NO: 3 (FIG. 5);

(b) DNA sequences comprising the nucleotide sequence as given in SEQ ID NO: 2 (FIG. 4);

(c) DNA sequences comprising a nucleotide sequence which hybridizes with a complementary strand of a nucleotide sequence of (a) or (b); and (d) DNA sequences comprising a nucleotide sequence which is degenerate to a nucleotide sequence of (c); and (ii) the amyloid precursor protein (APP) or its proteolytic product (Aβ), a functional part thereof or a protein functional equivalent to APP or Aβ or any mutated versions thereof, e.g., the exogenous or heterologous DNA sequence can be selected from the group consisting of (a) DNA sequences comprising a nucleotide sequence encoding the amino acid sequence as given in SEQ ID NO: 5 (FIG. 7);

(b) DNA sequences comprising the nucleotide sequence as given in SEQ ID NO: 4 (FIG. 6);

(c) DNA sequences comprising a nucleotide sequence which hybridizes with a complementary strand of a nucleotide sequence of (a) or (b); and (d) DNA sequences comprising a nucleotide sequence which is degenerate to a nucleotide sequence of (c). And, the inventive vector can contain an inventive promoter region for each exogenous or heterologous DNA sequence of (i) and (ii), or a promoter region for both (i) and (ii), i.e., an inventive promoter may drive expression of more than one exogenous or heterologous DNA sequence; and if desired, this can be exploited in any suitable arrangement in an inventive vector.

The vector can further comprise a selectable marker, preferably pha-1.

The invention also comprehends a cell transformed with at least one inventive isolated nucleic acid molecule, e.g., recombinant DNA molecule or at least one vector; and, the cell can be a prokaryotic or a eukaryotic cell. And, the cell can be in an animal, such as a non-human animal, such that the invention comprehends transgenic animals.

The inventive transgenic non-human animal can have a neuronal disorder. The neuronal disorder can be caused by a mutant sel-12 gene or a gene which is homologous to the sel-12 gene. The neuronal disorder-can caused by the expression of at least one inventive isolated nucleic acid molecule, e.g., recombinant DNA molecule, or at least one inventive vector. The animal, e.g., transgenic non-human animal, can be any desired species, for instance, from fruit fly to mammal, e.g., any suitable invertebrate or vertebrate, such as a nematode, e.g., C. elegans, or a mammal, e.g., a laboratory animal such as felines (such as domesticated cats or kittens), canines (such as domesticated dogs or puppies), rodents (such as mice, rabbits, gerbils, rats and the like), ruminants (such as sheep, goats and bovines and the like), primates (monkeys, apes and the like), inter alia.

In the aforementioned inventive methods or uses the chemical or biological substance can be selected from the group consisting of peptides, proteins, nucleic acids, antibodies, small organic compounds, hormones, neurotransmitters, peptidomimics and PNAs; and, the neuronal disorder can be Alzheimer disease.

The invention further comprehends the use of at least one inventive isolated nucleic acid molecule, e.g., recombinant DNA molecule, for inducing a neuronal disorder in a non-human. animal; for instance, the use of at least one inventive isolated nucleic acid molecule, e.g., recombinant DNA molecule, for the preparation of a pharmaceutical composition for inducing a neuronal disorder in a non-human animal. In these embodiments the exogenous or heterologous DNA sequence can encode a mutated version of a protein which has lost its capability of complementation of a sel-12 mutant phenotype. The neuronal disorder can be uncoordinated behavior and/or lethargic movement. And, the animal can be any desired species, for instance, from fruit fly to mammal, e.g., any suitable invertebrate or vertebrate, such as a nematode, e.g., C. elegans, or a mammal, e.g., a laboratory animal as discussed above.

In addition, since the inventive promoter region can confer expression in neural cells, advantageously all neural cells, and preferably at all stages of development, the at least one isolated nucleic acid molecule or nucleotide sequence, e.g., a heterologous DNA sequence (operatively linked to the promoter region) can encode a beneficial biological product such that the inventive combination of the promoter region and isolated nucleic acid molecule can be employed for numerous treatments or therapies, e.g., for treatment or therapy of neuronal disorders (e.g., uncoordinated behavior, lethargic movement, Alzheimer disease, inter alia); for instance, for the introduction into human or animal individuals or populations of missing genes or parts thereof, or of genetic material for modification, replacement or repair of defective genes.

The invention thus comprehends vectors, cells and tranogenic animals, such as mammals (including humans) containing such an inventive promoter region and isolated nucleic acid molecule combination, as well as compositions containing such an inventive combination or vectors or cells for delivery to an animal for purposes of such treatments or therapies, and treatment or therapeutic methods employing the inventive combination or vectors or cells comprising administering such to an individual in need of such treatment or therapy; and, the animal can be pre-natal or post-natal, e.g., a treatment or therapy can be in an individual after birth or in a mature individual or prior to birth. This type of therapy or treatment can be effected by any suitable vector; and by gene therapy one can introduce the inventive combination in vivo into cells using a retroviral vector (Naldini et al., Science 272 (1996), 263–267; Mulligan, Science 260 (1993), 926–932) or another appropriate vector. In genetic diseases the introduction of a normal or a functionally adequate gene or portion thereof represents gene replacement therapy, which can be applicable to numerous disorders, such as recessive disorders. A pharmaceutical composition for such treatment or therapy can be administered to the mammal at a suitable dose, which can be determined from this disclosure and knowledge in the art, without undue experimentation by the skilled artisan taking into consideration typical factors such as the species, age, sex, weight, condition and genetics of the mammal, the route of administration, whether the treatment is pre-natally or post-natally, toxicity, inter alia.

Furthermore, in view of the foregoing, in vitro, use of the inventive promoter region, especially in combination with at least one isolated nucleic acid molecule or nucleotide sequence, e.g., a heterologous DNA sequence (operatively linked to the promoter region) may also be within the invention. Such in vitro uses can be to have in vitro expression of gene products from neural cells for subsequent use for administration to an animal, e.g., for treatment or therapy (e.g., of neuronal disorders), or for creating neural cells expressing gene products for subsequent infusion or reinfusion into an animal (ex vivo treatments or therapies, e.g., of neuronal disorders); and, the invention thus may also comprehend compositions and methods employing such in vitro expressed gene products or such in vitro created cells (e.g., a pharmaceutical composition comprising such gene products or cells, or a method for treating a neuronal disorder comprising administering the gene products, cells, or composition containing such).

These and other embodiments are disclosed or are obvious from and encompassed by, the following Detailed Description.

BRIEF DESCRIPTION OF THE FIGURES

This disclosure may best be understood in conjunction with the accompanying drawings, incorporated herein by reference, wherein:

FIG. 8 shows a 20 bp synthetic linker (AATCGGATCCATGGCTTCAC; SEQ ID NO: 6) which replaced nucleotides 960–970 of SEQ ID NO: 1 (FIG. 3) including the sel-12 translational start codon [15]; and, FIGS. 9 and 10 show primers 5'-CCGAATTCTGTCCGAAAGGTCCA-3' (SEQ ID NO: 7) and 5'-CCGGATCCCTAGGTTGTGTTCCAGTC-3' (SEQ ID NO:8) for PCR amplification of the coding region of PS-1 by standard methods [39] to produce a fusion protein of maltose-binding protein and the large loop of PS-1.

DETAILED DESCRIPTION

Levitan [20] examined the expression pattern of transgenic $C.$ $elegans$ lines carrying a sel-12/lacZ chimeric reporter gene. However, it was found that this chimeric gene was only expressed in a subset of neural cell types during development.

In accordance with the present invention, a promoter region comprising the regulatory sequences driving expression of a heterologous nucleic acid molecule, e.g., a DNA sequence, in neural cells, advantageously substantially all neural cells, preferably at substantially all stages of development has been identified. Thus, this promoter is suitable to drive the expression of a heterologous DNA sequence in the above-mentioned cells. This allows studying the function and interaction of proteins which are expressed in the nervous systems of, for example, humans and the malfunction, and/or unregulated expression of which is supposed to be the causative agent of neuronal diseases.

Thus, the promoters of the invention are particularly suited and useful for the use and the engineering of transgenic non-human animals from fruit flies to mammals, e.g., any desired invertebrate or vertebrate such as nematodes, e.g., C. elegans, or mammals, e.g., laboratory animals such as felines (such as domesticated cats or kittens), canines (such as domesticated dogs or puppies), rodents (such as mice, rabbits, gerbils, rats and the like), ruminants (such as sheep, goats and bovines and the like), primates (monkeys, apes and the like), inter alia, which can serve as a test system for the development of drugs for the treatment of neuronal diseases.

In the context of the present invention the term "sel-12 promoter" means the promoter region of the sel-12 gene of C. elegans including the regulatory sequences which confer the specific expression of a heterologous DNA sequence in all neural cells preferably at all stages of development in C. elegans.

And, the term "nucleotide sequence" as used herein can mean nucleic acid molecule. Thus, a nucleotide sequence can be an isolated nucleic acid molecule, e.g., exogenous or a heterologous DNA. Similarly, the term DNA sequence can mean a DNA molecule, e.g., an isolated DNA molecule, e.g., an isolated exogenous or heterologous DNA molecule.

Figures 2, 3, 3A, 3B, 3C, 3D, 3E, 3F, 3G, 3H, 3I, 3J, 3K:
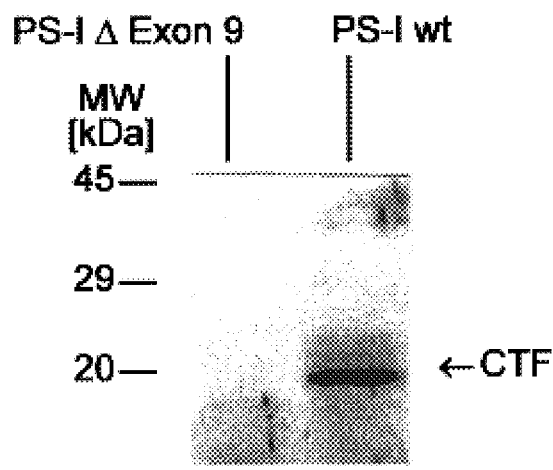
FIG. 2 shows proteolytic processing of human PS-1 in $C.$ $elegans$ (Protein extracts of lines transgenic for PS-1 Δexon9 or wild type PS-1 were immunoprecipitated with an antibody to the large loop of PS-1 and separated on a 12% polyacrylamide gel. The 20 kDa CTF was detected by immunoblotting using antibody 3027. Note the absence of the CTF in lines transgenic for PS-1 Δekon9. Due to the abundance of heavy and light chains in the immunoprecipitations, full length PS-1 can not be detected in the blots. In situ immuno-histochemistry was used to verify equivalent expression levels of PS-1 and PS-1 Δexon9. In non-transgenic lines the CTF was not detected)
FIG. 3 shows the nucleotide sequence of the DNA fragment containing the sel-12 promoter and regulatory sequences (SEQ ID NO: 1)

In accordance with the present invention, it was shown for the first time that the expression of a heterologous DNA sequence under the control of said promoter region occurs in all neural cells at all stages of development in C. elegans. The genomic DNA of C. elegans comprising the sel-12 promoter sequences is located on chromosome III (Wilson, Nature 368 (1994), 32–38) and the nucleotide sequence is available in the Genebank Database under accession No. U 41540. Cosmid F35H12 containing the genomic DNA including the sel-12 promoter can be obtained from Sanger Centre, Alan Coulson, Hinxton Hall, Cambridge CB10 IRQ, UK. The Genebank Database indicates the predicted coding region of the sel-12 gene. The nucleotide sequence of the DNA fragment containing the sel-12 promoter and regulatory sequences is depicted in FIG. 3 (SEQ ID No. 1). The ATG is located at position 960. The ATG is transpliced to a SL1 leader which then provides the 5' end comprising the transcriptional start nucleotide [37].

The term "promoter" refers to the nucleotide sequences necessary for transcription initiation, i.e. RNA polymerase binding, and also includes, for example, the TATA box. The term "regulatory sequences" refers to sequences which influence the specificity and/or level of expression, for example in the sense that they confer cell and/or tissue specificity. Such regions can be located upstream of the transcription initiation site, but can also be located downstream of it, e.g., in transcribed but not translated leader sequences.

The term "promoter region of a gene homologous to the sel-12 gene" also includes promoter regions and regulatory sequences of a gene from another species, for example, nematodes which is homologous to the sel-12 gene of C. elegans and which have the same expression pattern. Such promoters are characterized by their capability of conferring expression of a heterologous DNA sequence in all neural cells preferably at all stages of development. Thus, according to the present invention, promoters from other species can be used that are functionally homologous to the regulatory sequences of the promoter of the sal-12 gene from C. elegans, or promoters of genes that display an identical pattern of expression, in the sense of being expressed in neural cells preferably at all stages of development.

It is possible for the person skilled in the art to isolate with the help of the known sel-12 gene from C. elegans, corresponding genes from other species, for example, nematodes. This can be done by conventional techniques known in the art, for example, by using the sel-12 gene as a hybridization probe or by designing appropriate PCR primers. It is then possible to isolate the corresponding promoter region by conventional techniques and test it for its expression pattern. For this purpose, it is, for instance, possible to fuse the promoter to a reporter gene, such as luciferase or green fluorescent protein (GFP) and assess the expression of the reporter gene in transgenic C. elegans.

The present invention also relates to the use of promoter regions which are substantially identical to the sel-12 promoter of C. elegans or to a promoter of a homologous gene or to parts thereof and which are able to confer specific expression in all neural cells, preferably at all stages of development in C. elegans.

Such promoters differ at one or more positions from the above-mentioned promoters but still have the same specificity, namely they comprise the same or similar sequence motifs responsible for the above described expression pattern. Preferably such promoters hybridize to one of the above-mentioned promoters, most preferably under stringent conditions. Particularly preferred are promoters which share at least 85%, more preferably 90–95%, and most preferably 96–99% sequence identity with one of the above-mentioned promoters and have the same specificity. Such promoters also comprise those which are altered, for example by deletion(s), insertion(s), substitution(s), addition (s), and/or recombination(s) and/or any other modification(s) known in the art either alone or in combination in comparison to the above-described nucleotide sequence. Methods for introducing such modifications in the nucleotide sequence of the promoter of the invention are well known to the person skilled in the art. It is also immediately evident to the person skilled in the art that further regulatory sequences may be added to the promoter of the invention. For example, transcriptional enhancers and/or sequences which allow for induced expression of the promoter of the invention may be employed. A suitable inducible system is for example tetracycline-regulated gene expression as described, e.g., by Gossen and Bujard (Proc. Natl. Acad. Sci. USA 89 (1992), 5547–5551) and Gossen et al. (Trends Biotech. 12 (1994), 58–62). The expression of the sel-12 promoter of the invention may not be limited to the above-described specificity but may also occur in, e.g., muscle cells, including the pharyngeal, vulva and intestinal muscles, and vulva cells at all or different stages of development.

In a preferred embodiment of the present invention, the promoter comprises the nucleotides 468 to 959 and most preferably nucleotides 1 to 959 of the nucleotide sequence as set forth in FIG. 3 (SEQ ID No. 1) or a fragment thereof, which still confers expression in all neural cells, preferably at all stages of development.

The term "heterologous" with respect to the DNA sequence being operatively linked to the promoter of the invention means that said DNA sequence is not naturally linked to the promoter of the invention.

In a preferred embodiment the heterologous DNA sequence linked to the sel-12 promoter encodes a protein which is involved in neural development and/or diseases such as NOTCH involved in the development of various cancers (e.g. nasopharyngeal and mammary cancer). Preferably said disease is Alzheimer's Disease.

In a preferred embodiment the heterologous protein is Presenilin, a functional part thereof or a protein which is functionally equivalent to Presenilin. In this context, as as used throughout this specification "functional equivalent" or "functional part" of a protein means a protein having part or all of the primary structural conformation of the wild type protein possessing at least one biological property of said protein. The functional part of said protein or the functionally equivalent protein may be a derivative of the wild type protein by way of amino acid deletion(s), substitution(s), insertion(s), addition(s) and/or replacement(s) of the amino acid sequence. Also comprised by the term "functional" protein is the capability of said protein or part thereof to generate a specific immune response such as an antibody response.

Levitan [20] provided evidence that the expression of human Presenilin in the vulva precursor cells of *C. elegans* can functionally substitute sel-12 with respect to correct execution of egg-laying behavior of *C. elegans*. However, as set forth above, the promoter employed in Levitan [20] is only expressed in a minor fraction of neural cell, and is, therefore, not adequate to study the functional interaction of sel-12/Presenilin in nerve cell tissues, which is a prerequisite for the correct assessment of the biological function of such proteins and mutated versions thereof. Thanks to the present invention, it is now possible to express Presenilin in all neural cells and to fully substitute sel-12 function. This means that the expression of Presenilin under the control of the promoter of the invention cannot only complement the egg-laying defect effects, but also uncoordinated behavior and lethargic movements of sel-12 mutants, i.e. phenotypes which much more closely resemble that of human Alzheimer's disease. It has been argued that Presenilin mutants are a gain-of-misfunction mutants, explaining their dominant transmission. On the other hand, sel-12 mutants behave fully recessive. By overexpressing Presenilin mutants from the sel-12 promoter of the invention, this question can now be answered. Either Presenilin mutants overexpression results in a new phenotype (and is a gain-of-misfunction) or does not result in a new phenotype (and is a loss-of-function).

Figure 4:
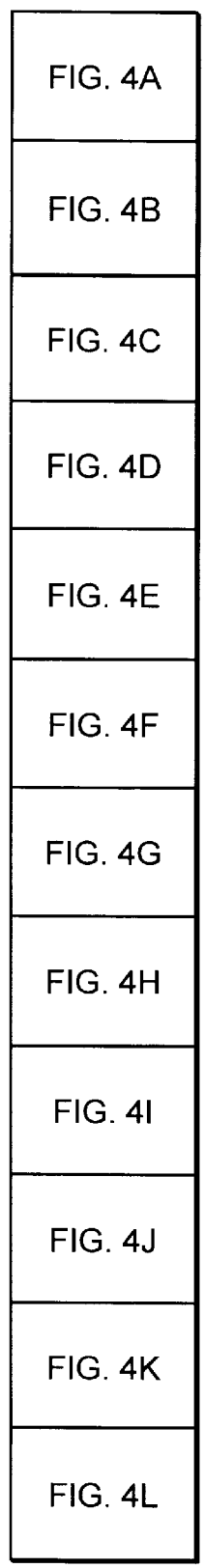
FIG. 4 shows a DNA sequence encoding Presenilin and an amino acid sequence therefor (SEQ ID NO: 2)
Figures 5, 5A:
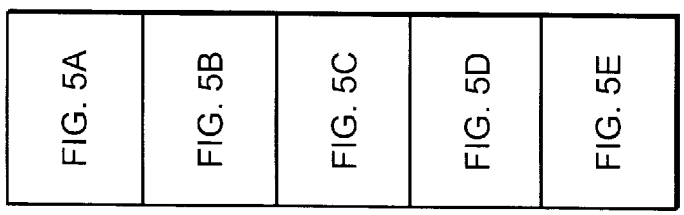
FIG. 5 shows an amino acid sequence for Presenilin (SEQ ID NO: 3)

In a particularly preferred embodiment, Presenilin is encoded by a DNA sequence selected from the group consisting of
(a) DNA sequences comprising a nucleotide sequence encoding the amino acid sequence as given in FIG. 5 (SEQ ID No.: 3);
(b) DNA sequences comprising the nucleotide sequence as given in FIG. 4 (SEQ ID No.: 2);
(c) DNA sequences comprising a nucleotide sequence which hybridizes with a complementary strand of a nucleotide sequence of (a) or (b); and
(d) DNA sequences comprising a nucleotide sequence which is degenerate to a nucleotide sequence of (c).

In another preferred embodiment the heterologous DNA sequence linked to the sel-12 promoter encodes the amyloid precursor protein (APP) or its proteolytic product (Aβ), a functional part thereof, or a protein functional equivalent to APP or Aβ or a mutated version thereof. *C. elegans* is a truly advantageous model system to study Alzheimer's Disease, if the functional relationship between Presenilin on one hand and APP or Aβ on the other hand can be studied. Since Alzheimer is a disease of the nervous system, it is obvious that APP/Presenilin interactions must be studied in the nervous system, where both proteins are expressed ubiquitously in humans. It is now possible to study whether Presenilin and SEL protein share, besides their functional relationship, also the ability to interact with APP or Aβ or mutant versions thereof. For this purpose, either expression of APP or Aβ under the control of the promoter of the invention in, e.g., *C. elegans* alone or a co-expression of Presenilin wild-type and mutants and APP in transgenic non-human animals both directed by the same promoter would be desirable to study their interaction. The functional interaction between presenilin and APP is regarded as one of the main targets for drug development against Alzheimer's disease. Due to the present invention, it is now possible to express both genes from the sel-12 promoter in all neural cells of *C. elegans* at all developmental stages.

Figure 6:
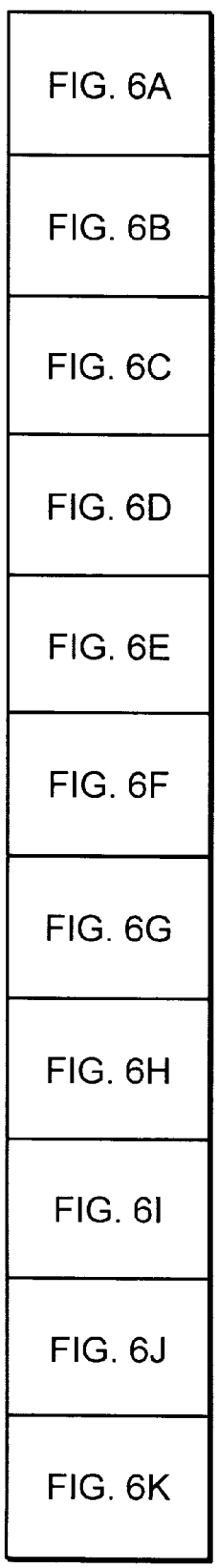
FIG. 6 shows a DNA sequence encoding APP or Aβ and an amino acid sequence therefor (SEQ ID NO: 4)
Figure 7:
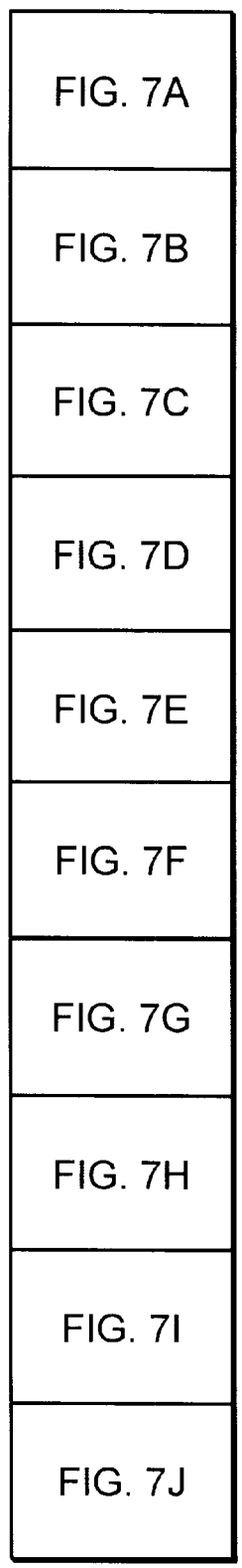
FIG. 7 shows an amino acid sequence for APP or Aβ (SEQ ID NO: 5)

In a particularly preferred embodiment of the invention APP or Aβ is encoded by a DNA sequence selected from the group consisting of
(a) DNA sequences comprising a nucleotide sequence encoding the amino acid sequence as given in FIG. 7 (SEQ ID No.: 5);
(b) DNA sequences comprising the nucleotide sequence as given in FIG. 6 (SEQ ID No.: 4);
(c) DNA sequences comprising a nucleotide sequence which hybridizes with a complementary strand of a nucleotide sequence of (a) or (b); and
(d) DNA sequences comprising a nucleotide sequence which is degenerate to a nucleotide sequence of (c).

In another preferred embodiment, the DNA sequence being operatively linked to a promoter of the invention encodes a mutated version of the afore-described proteins. This may be for example mutant forms of human Presenilin such as, for example, those described in [1to 7].

It is also to be understood that the heterologous DNA sequence operatively linked to the-promoter of the invention may encode an antisense RNA or a ribozyme targeted to a desired gene. In this embodiment the recombinant DNA of the invention molecules may be used for the suppression of the expression of a gene which is active in neural cells.

In another embodiment, the present invention also relates to vectors, particularly plasmids, cosmids, viruses, bacteriophages used conventionally in genetic engineering that contain a DNA molecule of the invention. Methods for making plasmids, cosmids, viruses, bacteriophages and the like are known such that the invention can be practiced by the skilled artisan from this disclosure and the knowledge in the art without undue experimentation [41].

In a preferred embodiment said vector comprises a DNA molecule wherein Presenilin, a functional part thereof or a protein which is functionally equivalent to Presenilin is operatively linked to the sel-12 promoter of the invention and a DNA molecule wherein the sel-12 promoter of the invention controls the expression of the APP or Aβ or a functional part thereof or a protein functionally equivalent to APP or Aβ or a mutated version thereof. This embodiment is particularly useful for studying the interaction of Presenilin and APP and/or mutants of both proteins.

In a particularly preferred embodiment, said vector further comprises a selectable marker preferably pha-1 [26]. In experiments performed in accordance with the present invention a Pha-1 expression plasmid (pBX) was used as a cotransformation marker. The complementation of pha-1 phenotype by pBX expression is 100% penetrant. All animals surviving at the restrictive temperature of 20° C. or 25° C. are transformed, allowing for a natural selection of transformed animals. Therefore, enrichment of any number of animals for performing biochemical studies, e.g. to follow PS-1 proteolysis, can be easily accomplished. This major advantage allows to perform immunoprecipitation experiments proving that PS-1 is proteolytically cleaved in *C.*

*elegans* like in human cells. Furthermore, a single observation at a fixed time point (e.g. 36 hours) is sufficient to monitor the function of the protein. Genetically crossing pha-1 into sel-12 mutants may not affect the sel-12 phenotype as described in the lin-12·smg–1 system of Levitan et al. [20].

Furthermore, the present invention relates in another embodiment to host cells transformed with recombinant DNA molecules as described above comprising the sel-12 promoter of the invention and linked thereto a DNA sequence as described above. The host cells can be prokaryotic, for example bacterial, or eukaryotic, for example fungal or animal cells.

Moreover, the present invention relates to a pharmaceutical composition comprising at least one of the aforementioned recombinant DNA molecules or vectors of the invention, either alone or in combination, and optionally a pharmaceutically acceptable carrier or excipient. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g. by intravenous, intraperitoneal, subcutaneous, intramuscular, topical or intradermal administration. Such compositions can be administered to a subject or patient in need of such administration in dosages and by techniques well known to those skilled in the medical, nutritional or veterinary arts taking into consideration the data herein, and such factors such a skilled artisan typically considers such as the age, sex, weight, genetics and condition of the particular subject or patient, and the route of administration, and toxicity (e.g., $LD_{50}$).

The present invention also relates to diagnostic compositions or kits comprising at least one of the aforementioned recombinant DNA molecules or vectors, and in the case of diagnostic compositions, optionally suitable means for detection.

Said diagnostic compositions may be used for methods of detecting and isolating promoters which are a functionally equivalent to the sel-12 promoter of the invention. The kits of the invention may further contain compounds such as further plasmids, antibiotics and the like for screening transgenic animals and/or *C. elegans* laboratory strains (e.g. pha-1 mutant animals) useful for the genetic engineering of non-human animals, preferably nematodes and most preferably *C. elegans*.

In a further embodiment, the present invention relates to a transgenic non-human animal comprising either in a form extrachromosomally or stably integrated into its genome a DNA molecule or a vector of the invention such that the presence of said DNA molecule or vector leads to the transcription and/or expression of the heterologous DNA sequence by the promoter of the invention.

In a preferred embodiment, the transgenic non-human animal has a neuronal disorder, preferably a neuronal disorder which is caused by a mutant sel-12 gene, or a gene which is homologous to the sel-12 gene.

In another preferred embodiment the neuronal disorder is caused by the expression of a DNA sequence encoding a protein involved in neuronal development and/or diseases as described above under the control of the sel-12 promoter of the invention.

In a particularly preferred embodiment said transgenic non-human animal is *C. elegans*. In *C. elegans*, defective SEL-12 protein in the HSNs, the vulva or in the somatic gonad can account for the Egl phenotype of sel-12 mutant animals [21, 22]. Levitan et al. recently showed that PS-1 expressed from the lin-12 promoter suppresses the Egl defect of sel-12(ar131) [20]. lin-12 expression in the nervous system has only been described in a discrete subset of cells in the ventral cord of L1 larvae [23]. Therefore, expression of SEL-12 or PS-1 in the somatic gonad and vulva is probably sufficient for rescuing the Egl phenotype. Since sel-12 is expressed in many more cell types than those involved in controlling the egg-laying behavior, it is conclusive that the defects caused by mutant SEL-12 may be rather subtle in other cells. Defects in the nervous system or in muscles are most likely responsible, e.g., for the lethargic movements of the sel-12 mutant animals. *C. elegans* sel-12 mutants suppress a hyper-active lin-12/ Notch variant, and their phenotype is reminiscent of the Egl phenotype caused by reducing lin-12 activity. It had therefore been suggested that *C. elegans* sel-12 is either directly involved in lin-12/ Notch signaling or in the receptor transport or recycling.

With the sel-12 promoter of the invention, it is now possible to study whether the human wild-type Presenilin gene rescues all defects of mutant *C. elegans* sel-12 and whether human Presenilin is likewise involved in the NOTCH mediated cell signaling pathway. Furthermore, since human Presenilin genes seem to have different functions in different stages of development, it is now possible to determine domains of the Presenilin protein which may be important for its biological activity and/or for the regulation of its activity. In addition, it is now possible to study mutations which effect different functional or regulatory aspects of Presenilin.

Methods for the production of sel-12 mutant *C. elegans* are known in the art, for example, targeted inactivation of sel-12 using the knock-out method described in Zwaal [35]. Both a complete gene inactivation and a deletion mutant can be constructed with this method. The Egl phenotype of a deletion mutant indicates a successful inactivation of gene function. The person skilled in the art can also employ a genetic screen to suppress a hyper-active lin-12/ Notch allele. This was the method which originally resulted in the cloning of sel-12 gene [15]. In theory, mutations in genes other than sel-12 could result in a phenotypically similar phenotype. Therefore, the position of the newly identified mutations has to be mapped using standard techniques [34]. Furthermore, starting with a given sel-12 mutant, a non-complementation screen can be carried out to identify new alleles of sel-12 [34].

Moreover, the present invention relates to a method for the identification of a chemical and/or biological substance capable of complementing a neuronal disorder comprising
  (a) contacting a transgenic non-human animal of the invention with a plurality of compounds; and
  (b) determining those compounds which are capable of complementing the neuronal disorder of the transgenic non-human animal.

Said plurality of compounds may be comprised in, for example, samples, e.g. cell extracts from, e.g. plants, animals or microorganisms. Furthermore, said compounds may be known in the art but hitherto not known to be capable of complementing a neuronal disorder. The plurality of compounds may be, e.g., added to the culture medium or injected into the animals. The term "plurality of compounds" in a method of the invention is meant to be understood as a plurality of substances which are either identical or not. If a sample containing a plurality of compounds is identified in the method of the invention, then it is either possible to isolate the compound from the original sample identified as containing the compound capable of complementing the neuronal disorder of the transgenic non-human animal, or one can further subdivide the original sample, for example, if it consists of a plurality of different compounds, so as to reduce the number of different substances per sample and repeat the method of the subdivisions of the original sample. Depending on the complexity of the samples, this can be done several times, preferably until the sample identified according to the method of the invention only comprises a limited number of substances. Preferably said sample comprises substances of similar chemical and/or physical properties, most preferably said substances are identical.

Determining whether a compound is capable of complementing a neuronal disorder can be done by, for example, in C. elegans by monitoring the egg-laying properties and behavior of the transgenic non-human animals of the invention contacted with the compounds compared to that of wild-type animals or compared to a transgenic non-human animal contacted with a compound which is either known to be capable or incapable of complementing the neuronal disorder of said transgenic non-human animal of the invention. Furthermore, the person skilled in the art can monitor the physical behavior, or for example the movement, and/or the brood size of the above-described animals. Such methods are well known in the art and are described in, for example Epstein [38].

In a further embodiment, the present invention relates to a method for the identification of a chemical and/or biological substance capable of interfering Presenilin/APP interaction comprising (a) contacting a transgenic a non-human animal of the invention with a plurality of compounds; and (b) determining those compounds which are capable of interfering with Presenilin/APP interaction.

As discussed herein, the interaction of PS and APP or its precursor Aβ play an important role in the onset of Alzheimer's disease. Transgenic non-human animals expressing Presenilin and the APP gene and/or mutated versions thereof under the control of the sel-12 promoter of the invention can now be used for the identification of substances, which, for example, are capable of restoring the wild-type interaction of mutated Presenilin and APP proteins. Some genetic changes lead to altered protein conformational states. For example, human presenilins have been suggested to be part of the transport machinery of the cell. Genetic changes may therefore result in a decreased activity of the protein transporters. Restoring the activity of mutant presenilin protein or increasing the activity of other proteins which interact with mutant presenilin proteins is the most elegant and specific means to correct these molecular defects. In addition, some genetic changes may result in altered conformational states of the protein. This, in turn, may functionally inactivate the presenilin, making it incapable of complementing sel-12 mutants described in [20]. In order to restore the function of such mutant proteins an antibody may be used which bind to an epitope and induce a conformational change of the protein thereby restoring the wild type function. Thus, the methods of the invention are also useful to screen e.g., antibody, Fab or Fv expression libraries wherein the DNA sequence encoding said antibodies or derivatives thereof are under the control of the promoter of the invention.

It is, of course, evident to the person skilled in the art that also other protein or peptide expression libraries using the promoter of the invention may be employed.

Further, the present invention relates to the use of a transgenic non-human animal of the invention for identifying a substance capable of complementing a neuronal disorder, said use comprising administering a substance to said transgenic non-human animal determining whether a substance complements the physical and/or behavioral disorder displayed by said transgenic non-human animal.

In a preferred embodiment, the chemical or biological substance used in the methods and uses of the invention is selected from the group consisting of peptides, proteins, nucleic acids, antibodies, small organic compounds, hormones, neural transmitters, peptidomimics, PNAs (Milner, Nature Medicine 1 (1995), 879–880; Hupp et al., Cell 83 (1995), 237–245; Gibbs and Oliff, Cell 79 (1994), 193–198).

In a further embodiment, the invention relates to the use of a DNA molecule or vector of the invention or a substance identified by a method of the invention for the preparation of a pharmaceutical composition for treating, preventing and/or delaying a neuronal disorder in a subject, preferably wherein the neuronal disorder is Alzheimer's Disease.

In a further embodiment, the present invention relates to the use of DNA molecule of the invention wherein the DNA sequence being operatively linked to the sel-12 promoter of the invention encodes a protein or mutated version thereof which is involved in neuronal diseases for preparation of a pharmaceutical composition for inducing a neuronal disorder in a non-human animal.

In a preferred embodiment, said neuronal disorder is uncoordinated behavior and lethargic movement.

In a most preferred embodiment of the methods and uses of the invention, said non-human animal is C. elegans.

A better understanding of the present invention and of its many advantages will be had from the following examples, given by way of illustration.

EXAMPLES

Example 1

Cloning and Modification of the sel-12 Constructs

Starting plasmid pBY115 equals pSPX4 [15] and contains a 3675 bp genomic SpeI/Xho fragment of cosmid F35H12 in Bluescript (Stratagene). To construct the expression plasmid pBY125 which bears all cis-regulatory sequences necessary for sel-12 expression in all neural cells, nucleotides 960–970 of SEQ ID NO: 1 (FIG. 3) including the sel-12 translational start codon [15] was replaced by a 20 bp synthetic linker (AATCGGATCCATGGCTTCAC; SEQ ID No.: 6; FIG. 8) which includes EcoRI, BamHI and NcoI restriction sites to facilitate cloning of cDNAs. Due to the deletion of this ATG, this plasmid does not express SEL-12. In order to determine the expression pattern of the sel-12 promoter, PS-1 and the green fluorescent protein (GFP) reporter-gene were expressed under the control of the sel-12 promoter. pBY140 is pBY125 with a PS-1 CDNA fragment [7] providing its own ATG and stop codons cloned into the.EcoRI site. cDNAs of the Δ9 exon mutant [7] was inserted into pBY140 to replace the wild type PS-1 coding region. pBY142 contains nucleotides 1-492 upstream of the sel-12 translational start (nucleotides 468 to 959 of SEQ ID NO: 1; FIG. 3) and the PS-1 wild type coding region or mutants, respectively. This fragment was fused to the unc54 3' UTR in pPD49.26 [24]. pBY142 does not contain any sequences downstream of the sel-12 ATG. Results obtained with pBY142 were identical to that obtained with pBY140.

The sel-12::GFP reporter gene was constructed by replacing the PS-1 coding region of pBY140 with a BamHI/PstI fragment containing an engineered GFP gene with optimized codon usage [25].

Example 2

Generation of Transgenic *C. elegans*

The procedure was based on a method published previously [26, 27]. The plasmid containing the sel-12 promoter controlling the expression of the Presenilin-1 or GFP was mixed at appropriate concentrations [27] with a marker gene. Several marker genes have been described and were either dominant (rol-6; [32]), or complement a mutant defect of the animals injected (pha-1: [26], lin-15: [33]). The DNA mix was injected into the gonad of young adult *C. elegans* animals. First generation progeny was transferred onto agarose plates and scored for marker expression, (dominant or rescue phenotype, respectively). Appropriate animals were selected and transferred to fresh plate. Second generation progeny which express the marker gene was generally semigtably transformed with both the marker gene and the sel-12 expression plasmid.

Example 3

Expression Pattern of the sel-12 Promoter

Figure 1A:
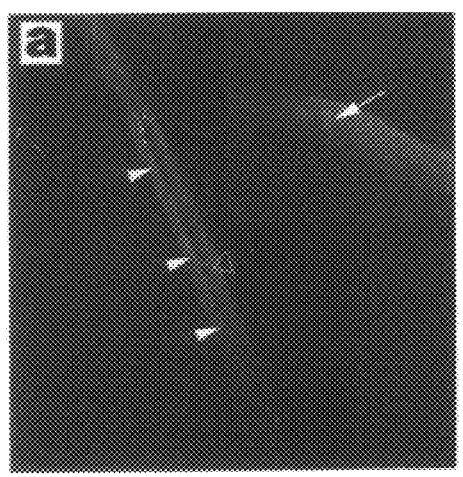
FIG. 1a to 1f show expression of sel-12 transgenes, monitored by PS-1 specific antibody staining (a,b) and GFP (c–f) ((a) L2 animal expressing PS-1 wild type protein (White Arrow heads: ventral nerve cord. Open arrow heads: ventral cord neurons. Inserted figure: Nerve ring neuropile in the head of an L3 animal. (b) L3 animal expressing PS-1 Δexon9. Same labeling as in (a). (c) Adult. Neurons in lateral (lg), ventral (vg) and anterior (ag) ganglion. Arrow: nerve ring. (d) Adult. tail neurons in lumbar ganglion (lg). ventral cord (vc) and dorsal cord (dc) processes. (e) Adult. vulva (vu) expression. GFP expression was also detected in the somatic gonad and the vulva muscles. White arrow head: CAN neuron. Arrow: HSN motoneuron which controls vulva contraction. (f) Late embryo: neuronal staining)
Figure 1B:
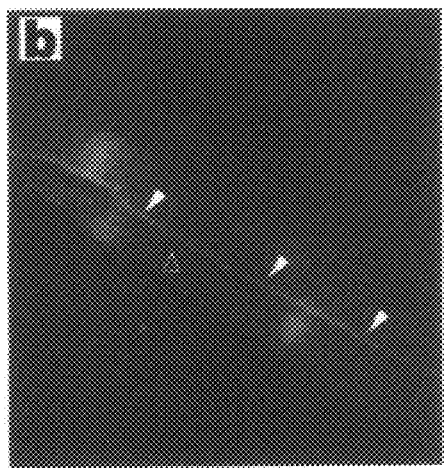
Figure 1C:
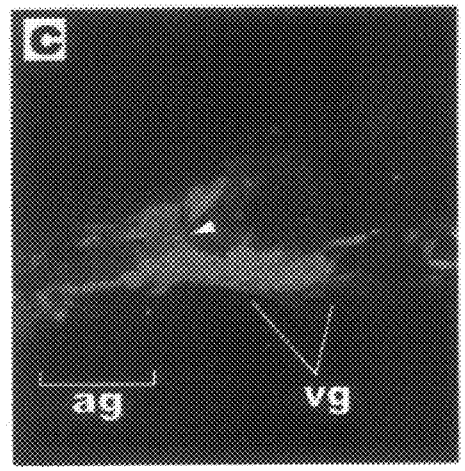
Figure 1D:
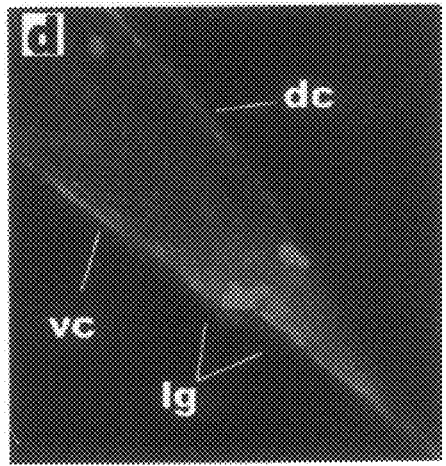
Figure 1E:
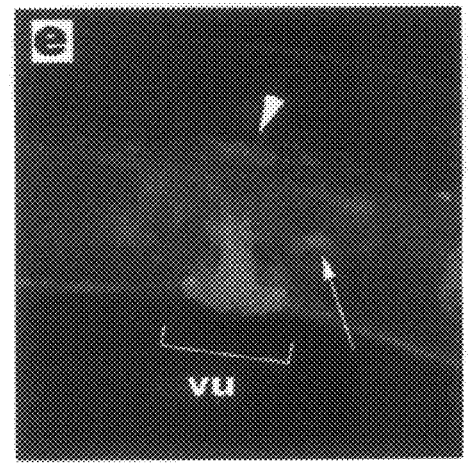
Figure 1F:
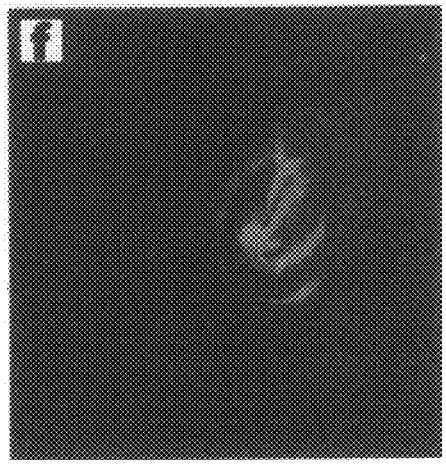

GFP expression was assessed in animals grown at 15° C. GFP staining was much more intense than PS-1 antibody staining, thus greatly facilitating the detection of expressing cells. To document GFP and PS-1 expression, photographs were taken at a Leica TCS NT confocal laser scanning microscope. Up to 8 levels of focus were photographed and merged into the pictures shown. Gut autofluorescence present in the GFP images was electronically subtracted. Nomarski DIC (differential interference-contrast) images of *C. elegans* were taken using a ZEISS Axiophot microscope with a Hamamatsu CID camera attached. Applicant monitored expression using PS-1 and Green Fluorescent Protein (GFP) reporter genes under the control of the sel-12 promoter. Expression of PS-1 was detected by PS-1-specific antibody 2953 [7] in many neural and muscle cells, in the vulva and in the somatic gonad. Expression was strongest in neurites and weaker in cell bodies, whereas nuclear staining was never observed (FIG. 1a, b). Staining with antibody 2953 was low compared to GFP, but was expressed in the same cells (FIG. 1a–f). The GFP variant used is targeted efficiently to the nucleus and the cytoplasm of cells, and therefore facilitated cell identifications, considerably. Expression was first observed at about 400 minutes after fertilization (comma stage) in many, if not all, cells and continues until adulthood. The sel-12 promoter directs expression in-most head, pharyngeal and tail neurons. In the central body region, mechanoreceptor neurons, the CAN neurons and a pair of serotonergic motoneurons (HSN) which control the egg-laying muscles were identified (FIG. 1e). Expression was also observed in many muscle cells, including the pharyngeal, vulva and intestinal muscles. In addition, most vulva cells express sel-12 in the fourth larval state (L4) (FIG. 1b).

Example 4

Expression of Mutant PB-1 Genes in *C. elegans*

Since FAD mutations are dominant, it had been suggested that mutations in presenilin proteins cause a neomorphic (gain-of-misfunction) phenotype. Applicant therefore injected high concentrations of plasmids expressing the human PS-1 gene and mutant PS-1 A246E in wild type animals and looked for dominant effects caused by the mutation. Steady-state levels of eggs in adult animals were determined as described [28]. Animals were singled at late L4 stage (crescent stage) and grown at 20° C., Eggs were counted under a ZEISS Telaval 31 microscope after 24, 36 and 70 hours. 2 days after they started to lay eggs, adults were picked individually again to determine their life-span and vitality.

Applicant also determined the developmental stages of embryos at egg-laying [22,28]. For this purpose, Applicant examined with a high magnification microscope (Zeiss Telaval 31) at least five freshly laid eggs or the five to ten eggs in the uterus closest to the vulva opening of all transgenic animals. Applicant grouped the developmental stages into four categories: one-to-eight cells, nine-cell to comma, postcomma to threefold, hatched larvae. Since embryonic development in each strain occurred at similar rates, differences between strains in this assay reflect different rates of egg laying [28]. To determine At their brood size, sel-12::PS-1 constructs were injected together with the dominant cotransformation marker pRF4 (rol-6(su1006)) [24] into sel-12(ar131) animals, and both roller and non-roller progeny was counted. Alternatively, animals transgenic for sel-12::PS-1 derivatives and pBX were grown at 15 OC and all progeny was counted. Animals transgenic for either PS-1 wild type or PS-1 A246E had an egg-laying phenotype indistinguishable from wild type animals (Table I). Their motility and behavior was also unaffected. Therefore, these results reveal no evidence for a gain-of-misfunction activity associated with FAD mutants. However, overexpressing of both PS-1 variants resulted in a decreased brood size of the transgenic animals (Table I). It is in this context interesting to note that some dominant alleles of lin-12 also have reduced brood sizes for reasons that are unknown [19]. Since Applicant has not been able to obtain transgenic lines using higher concentrations of PS-1 or sel-12 expression plasmids, Applicant suspects that overexpression of the presenilin proteins is toxic for *C. elegans*.

This example demonstrates that it is possible to express at least two genes from the sel-12 promoter of the invention and *C. elegans* and the usefulness of the system to study protein-protein interaction in vivo.

Example 5

Analysis of Proteolytic Processing of Presenilin in *C. elegans*

Recently, PS-1 was described to be proteolytically cleaved in the hydrophilic loop [12, 13]. The lack of endogenous full-length PS-1 suggests that the proteolytic fragments exhibit the biological function of PS-1. Moreover, a naturally occurring mutation which lacks exon nine [14] inhibits proteolytic processing and results in the accumulation of full-length PS-1 [12]. Applicant generated transgenic animals expressing the deletion and verified by in situ immunochemistry that PS-1 wild type and Δexon9 are expressed in similar amounts (see FIG. 1). Next Applicant analyzed proteolytic processing by immunoprecipitation. For this purpose, Applicant monitored the accumulation of a 20 kDa C-terminal fragment (CTF) which has been described as a processing product in mammalian cells and transgenic mice [10, 12, 13]. Applicant immunoprecipitated the 20 kDa CTF with the polyclonal antibody 3027 raised to the large loop of PS-1. Antibody 3027 was raised against the hydrophilic loop of PS-1 which is not conserved in the sel-12 sequence. Therefore, it does not cross-react with the *C. elegans* endogenous sel-12 protein. To produce a fusion protein of maltose-binding protein and the large loop of PS-1, the corresponding coding region of PS-1 was amplified by PCR according to-standard methods [39] using the following primers:

5'-CCGAATTCTGTCCGAAAGGTCCA-3' (SEQ ID NO: 7) and

5'-CCGGATCCCTAGGTTGTGTTCCAGTC-3' (SEQ ID NO:8) (FIGS. 9 and 10).

The PCR-products-were restricted with BamH1/EcoRI and cloned into pMAL-c2 (New England Biolabs). The fusion protein was expressed in *E. coli* DH5a and purified by chromatography using an amylose column. The purified protein was injected into rabbits as described [7]. Affinity purification was carried out as described [7]. Antibody specificity was analyzed in human kidney 293 cells transiently expressing PS-1 and PS-2 as well as in transgenic mice over-expressing PS-1. The antibody does not cross-react with PS-2 and identifies full-length PS-1 as well as the 20 kDa CTF. Identical peptides were detected with antibody$_{anti\ loop}$[12] which was recently used to show proteolytic processing of PS proteins in mammalian cells and transgenic mice [12]. For PS-1 antibody staining, animals were fixed and stained as described [29]. Cells were identified using the criteria described [29]. Immunoprecipitated PS-1 protein was then detected by western blotting using this antibody. *C. elegans* animals expressing wild type PS-1 accumulated the CTF indicating that PS-1 is processed in *C. elegans* in a similar way as in mice and humans. In contrast, no CTF was detected in animals expressing Δexon9 (FIG. 2). All PS-1 antibodies Applicant tested exhibit strong cross-reactivity with heavy and light chain immunoglobulins. Therefore, Applicant was not able to detect either full-length PS-1 or the amino-terminal fragment which comigrate in the Western blots. Nevertheless, Applicant's in situ antibody staining results and the detection of the PS-1 endoproteolytic product CTF clearly show that PS-1 is processed in *C. elegans* like in human cells.

TABLE I

Assessment of dominant phenotypes resulting from overexpression of PS-1 variants

| Genotype | concentration of injected DNA (ng/µl) | brood size | Egg laying behavior | eggs in utero |
|---|---|---|---|---|
| N2 wild type | — | 254 ± 42 | + | 17 ± 4 |
| N2 Ex(PS-1 wt)[1] | 25 | 80 ± 23 | + | 16 ± 6 |
| N2 Ex(PS-1 A246E)[1] | 25 | 85 ± 25 | + | 19 ± 6 |
| N2 Ex(pBY125 vector) | 25 | 237 ± 65 | + | 15 ± 6 |

Animals of at least five transgenic lines were analyzed. Brood size of at least 50 animals of each genotype were determined at 15° C.
Plasmids used for the expression of presenilin variants: PS-1 wt: pBY140; PS-1 A246E: pBY140 containing the respective point mutation; SEL-12 wt: pBY115. Egg laying behavior and egg counts were performed as outlined in the Examples.
[1]No transgenic lines were obtained after injection of DNA at higher concentrations.
N2 = wild-type *C. elegans* strain
Ex = N2 Expressing the indicated protein (_)
PS-1 wt = pBY140 plasmid containing the wild-type presenilin (PS-1) gene
PS-1 A246E = pBY140 plasmid containing a gene coding for a presenilin PS-1 gene which has a point mutation (Ala 246 to Glu) at amino acid 246
pBY125 vector = empty pBY125 plasmid
pBY125 = pBY115 plasmid wherein nucleotides 960–970 of the sel-12 gene (SEQ ID NO:1) were replaced with a 16 base pair synthetic linker (SEQ ID NO:6) which includes EcoRI, BamHI and NcoI restriction sites to facilitate cloning
pBY140 = pBY125 plasmid containing PS-1 cDNA
pBY115 = Bluescript plasmid (Stratagene) containing a 3675 bp genomic SpeI/Xho fragment of cosmid F35H12

The present invention is not to be limited in scope by its specific embodiments described herein which are intended as single illustrations of individual aspects of the invention and any embodiments, e.g., DNA moleucles, or vectors, which are functionally equivalent are within the scope of the invention. Indeed, various modifications of the invention in addition to those shown and described herein will become apparent to those skilled in the art from the foregoing description and accompanying drawings. These Modifications are intended to fall within the scope of the appended claims. Accordingly, having thus described in detail preferred embodiments of the present invention, it is to be understood that the invention defined by the appended claims is not to be limited to particular details set forth in the above description as many apparent variations. thereof are possible without departing from the spirit or scope of the present invention.

REFERENCES 1. van Broeckhoven, C. (1995) Presenilins and Alzheimer's disease. Nature Genetics 11, 230–232.
2. Sherrington, R., Rogaev, E. I., Liang, Y. Rogaeva, E. A., Levesque, G., Ikeda, M., Chi, H., Lin, C., Li, G., Holman, K., Tsuda, T., Mar, L., Foncin, J.-F., Bruni, A. C., Montesi, M. P., Sorbi, S., Rainero, I., Pinessi, L., Nee, L., Chumakov, I., Pollen, D., Brookes, A., Sansequ, P., Polinsky, R. J., Wasco, W., Da Silva, H. A. R., Haines, J. L., Pericak-Vance, M. A., Tanzi, R. E., Roses, A. D., Fraser, P. E., Rommens, J. M., & St. George-Hyslop, P. H. (1995) Cloning of the gene bearing missense mutations in early-onset familial Alzheimer's disease. Nature 375, 754–760.
3. Levy-Lahad, E., Wijsman, E. M., Nemens, E., Anderson, L., Goddard, K. A. B., Weber, J. L., Bird, T. D., & Schellenberg, G. D. (1995) Candidate gene for the chromosome 1 familial Alzheimer's disease locus. Science 269, 973–977.
4. Rogaev, E. I., Sherrington, R., Rogaeva, E. A., Levesque, G., Ikeda, M., Liang, Y., Chi, H., Lin, C., Holman, K., Tsuda, T., Mar, L., Sorbi, S., Nacmias, B., Piacentini, S., Amaducci, L., Chumakov, I., Cohen D., Lannfelt, L., Fraser, P. E., Rommens, J. M. & St. George-Hyslop, P. H. (1995) Familial Alzheimer's disease in kindred with missensense mutations in a gene on chromosome 1 related to the Alzheimer's disease type 3 gene. Nature 376, 775–778.
5. Haass, C. (1996) Presenile because of presenilin: the presenilin genes and early onset Alzheimer's disease. Current Opinion in Neurol. 9, 254–259.
6. Kovacs, D. M., Fausett, H. J., Page, K. J., Kim, T. -W., Moir, R. D., Merriam, D. E., Hollister, R. D., Hallmark, O. G., Mancini, R., Felsenstein, K. M., Hyman, B. T., Tanzi, R. E., & Wasco, W. (1996) Alzheimer's-associated presenilins 1 and 2: Neuronal expression in brain and localization to intracellular membranes in mammalian cells. Nature Medicine 2, 224–229.
7. Walter, J., Capell, A., Grünberg, J., Pesold, B., Schindzielorz, A., Prior, R., Podlisny, M. B., Fraser, P., St. George-Hyslop, P., Selkoe, D. J., & Haass, C. (1996) The Alzheimer's disease-associated presenilins are differentially phosphorylated proteins located predominantly within the endoplasmic reticulum. Molecular Medicine, 2, 673–691.
8. Cook, D., Sung, J., Golde, T., Felsenstein, K., Wojcyk, B., Tanzi, R., Trojanowski, J., Lee, V. & Doms, R. (1996) Expression and analysis of presenilin 1 in a human neuronal system: localization in cell bodies and dendrites Proc. Natl. Acad. Sci. USA 93, 9223–9228.
9. Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, 9. R., Wasco, W., Lannfelt, L., Selkoe, D., & Younkin, S. (1996) Secreted amyloid β-protein similar to that in the senile plaques of Alzheimer's disease is increased in vivo by the presenilin 1 and 2 and APP mutations linked to familial Alzheimer's disease. Nature Medicine 2, 864–870.

10. Duff, K. Eckman, C., Zehr, C., Yu, X., Prada, C. M., Perez-Tur, J., Hutton, M., Buee, L., Harigaya, Y., Yager, D., Morgan, D., Gordon, M.N., Holcomb, L., Refolo, L., Zenk, B., Hardy, J., & Younkin, S. (1996) Increased amyloid-β42 (43) in brains of mice expressing mutant presenilin 1. Nature 383, 710–713.

11. Younkin, S. (1995) Evidence that Aβ42 is the real culprit in Alzheimer's disease. Ann. Neurology 37, 287–288.

12. Thinakaran, G., Borchelt, D. R., Lee, M. K., Slunt, H. H., Spitzer, L., Kim, G., Ratovitsky, T., Davenport, F., Nordstedt, C., Seeger, M., Hardy, J., Levey, A. I., Gandy, S. E., Jenkins, N. A., Copeland, N. G., Price, D. L., & Sisodia, S. S. (1996) Endoproteolysis of presenilin 1 and accumulation of processed derivatives in vivo. Neuron 17, 181–190.

13. Mercken, M., Takahashi, H., Honda, T., Kazuki, S., Murayama, M., Nakazato, Y., Noguchi, K., Imahori, K. & Takashima, A. (1996) Characterization of human presenilin 1 using N-terminal specific monoclonal antibodies: evidence that Alzheimer's mutation affect proteolytic processing. FEBS Letters 389, 297–303.

14. Perez-Tur, J., Froelich, S., Prihar, G., Crook, R., Baker, M., Duff, K., Wragg, M., Busfield, F., Lendon, C., Clark, R. F., Roques, P., Fuldner, R. A., Johnston, J., Cowburn, R., Forsell, C., Axelman, K., Lilius, L., Houlden, H., Karran, E., Roberts, G.W., Rossor, M., Adams, M.D., Hardy, J., Goate, A., Lannfelt, L., & Hutton, M. (1995) A mutation in Alzheimer's disease destroying a splice acceptor site in the presenilin-1 gene. NeuroReport 7, 297–301.

15. Levitan, D. & Greenwald, I. (1995) Facilitation of lin-12-mediated signaling by sel-12, a Caenorhabditis elegans S182 Alzheimer's disease gene. Nature 377, 351–154.

16. L'Hernault, S., & Arduengo P. M. (1992) Mutation of a putative sperm membrane protein in *Caenorhabditis elegans* prevents sperm differentiation but not its associated meiotic divisions. J. Cell Biol. 119, 55–68.

17. Doan, A., Thiankaran, G., Borchelt, D. R., Slunt, H. H., Ratovitsky, T., Podlisny, M., Selkoe, D. J., Seeger, M., Gandy, S. E., Price, D. L., & Sisodia, S. S. (1996). Protein Topology of Presenilin 1. Neuron 17, 1023–1030.

18. Li, X., & Greenwald, I. (1996) Membrane Topology of the C. elegans SEL-12 Presenilin. Neuron 17, 1015–1021.

19. Greenwald, I. S., Sternberg, P. W., & Horvitz, H. R. (1983). The lin-12 locus specifies cell fates in *Caenorhabditis elegans*. Cell 34, 435–444.

20. Levitan, D., Doyle, T. G., Brousseau, D., Lee, M. K., Thinakaran, G., Slunt, H. H., Sisodia, S. S., & Greenwald, I. (1996) Assessment of normal and mutant human presenilin function in *Caenorhabditis elegans*. Proc. Natl. Acad. Sci. USA 93, 14940–14944.

21. Desai, C., Garriga, G., McIntire, S. L., & Horvitz, H. R. (1988) A genetic pathway for the development of the *Caenorhabditis elegans* HSN motor neurons. Nature 336, 638–646.

22. Trent, C., Tsung, N., & Horvitz, H. R. (1983) Egg-laying defective mutants of the nematode *C. elegans*. Genetics 104, 619–647.

23. Wilkinson, H. A., & Greenwald, I. (1995) Spatial and Temporal Patterns of lin-12 Expresssion During *C. elegans* Hermaphrodite Development. Genetics 141, 513–526.

24. Fire, A., White Harrison, S., & Dixon, D. (1990) A modular set of lacZ fusion vectors for studying gene expression in Caenorhabditis elegans. Gene 93, 189–198.

25. Haas, J., Park, E.-C., & Seed, B. (1996) Codon usage limitation in the expression of HIV-1 envelope glycoprotein. Curr. Biol. 6, 315–324.

26. Granato, M., Schnabel, H., & Schnabel, R. (1994) pha-1, a selectable marker for gene transfer in *C. elegans*. Nuci. Acids Res. 22, 1762–1763.

27. Mello, C. C., Kramer, J. M., Stinchcomb, D., & Ambros, V. (1991). Efficient gene transfer in *C. elegans*: extrachromosomal maintenance and integration of transforming sequences. EMBO J. 10, 3959–3970.

28. Koelle, M. R., & Horvitz, H. R. (1996) EGL-10 Regulates G Protein Signaling in the *C. elegans* Nervous System and Shares a Conserved Domain with Many Mammalian Proteins. Cell 84, 115–125.

29. Baumeister, R., Liu, Y., & Ruvkun, G. (1996) Lineage-specific regulators couple cell lineage asymmetry to the transcription of the *C. elegans* POU gene unc-86 during neurogenesis. Genes Dev. 10, 1395–1410.

30. Haass, C., Hung, A., & Selkoe, D. (1991) Processing of β-amyloid precursor protein in microglia and astrocytes favors an internal localization over constitutive secretion. J. Neuroscience 11, 3783–3793.

31. Sambrook et al. (1989) Molecular Cloning, A Laboratory Manual. second ed., DSH Press, Cold Spring Harbor. For hybridization techniques, reference is also made to "Nucleic Acid Hybridisation, A Practical Approach", Hames and Higgins eds., IRL Press, Oxford, 1985.

32. Fire, A. (1986) Integrative transformation of *Caenorhibditis elegans*. Embo J. 5, 10.

33. Huang, L. S., Tzou P. and Sternberg, P. W. (1994). The lin-15 locus encodes two negative regulators of Caenorhabditis elegans vulval development. Mol. Biol. Cell 5, 395–411.

34. Wood, W. B. (1988). The nematode *C. elegans*: Cold Spring Harbor Labroatory, Cold Spring Harbor, N.Y.).

35. Zwaal, R. R., Broeks, A., van Meurs, J., Groenen, J. T. M., and Plaster, R. H. A. (1993). Target-selected gene inactivation in *Caenorhabditis elegans* by using a frozen transposon insertion mutant bank. Proc. Natl. Acad. Sci. USA 90, 7431–7435.

36. Wilson et al. (1994). 2.2 Mb of contiguous nucleotide sequence from chromosome III of *C. elegans*. Nature 368, 32–38.

37. Krause, M. and Hirsh, D. (1987). Cell 49, 753–761.

38. Epstein, H. F., Shakes, D. C.(eds.) (1995). *Caenorhabditis elegans*, Modern Biological Analysis of an Organism, Academic Press, San Diego.

39. Innis, M. A., Gelfand, D. H., Sninsky, J. J. and White, T. J. (eds.) (1990). PCR Protocols, Academic Press, San Diego.

40. Marx, J., "ALZHEIMER'S RESEARCH, Dissecting How Presenilins Function—and Malfunction," Science Vol. 274, Number 592, Issue 13, December 1996, pp 1838–1840, The American Association for the Advancement of Science.

41. Methods for making a vector or recombinant can, for example in addition to those discussed in the foregoing text, be by or analogous to any of the methods disclosed in any of U.S. Pat. Nos. 4,603,112, 4,769,330, 5,174,993, 5,505,941, 5,338,683, 5,494,807, and 4,722,848, WO 95/30018, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, Dec., 1983, Vol. 3, No. 12, p. 2156–2165; Pennock et al., "Strong and Regulated Expression of *Escherichia coli* B-Galactosidase in Insect Cells with a Baculovirus vector," Molecular and Cellular Biology Mar. 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068-3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos 5,591,639, 5,589,466, and 5,580,859 relating to DNA expression vectors. While certain of the foregoing vectors or recombinants may not necessarily be applicable to neural cells, they may still be used in the practice of the invention if one desires to replicate the DNA of the inventive promoter region or of the inventive promoter region operative linked to a heterologous sequence, e.g., for purposes of creating additional copies thereof for subsequent use in a vector suitable for neural cells; and, methods in the foregoing documents may provide analogous techniques for preparing vectors suitable for neural cells.

42. Any antibodies or fragments thereof employed in any practice of the invention can additionally be obtained by using conventional methods which are described, e.g., in Harlow and Lane "Antibodies, A Laboratory Manual", CSH Press, Cold Spring Harbor, 1988. These antibodies may be monoclonal antibodies or comprised in polyclonal antisera or fragments thereof. Any antibody used in any practice of the invention, when appropriate, may be labeled with detectable tags such as a histidine flags or a biotin molecule, or the like, without any undue experimentation.

SEQUENCE LISTING

<160> NUMBER OF SEQ ID NOS: 8

<210> SEQ ID NO 1
<211> LENGTH: 4137
<212> TYPE: DNA
<213> ORGANISM: Caenorhabditis elegans

<400> SEQUENCE: 1

```
tgaaagttgt attaagattt acagctgtgt cagtgtcatt caaaaacatt ccatacattt      60
ttcaaacctt ccataacatt tcacaatttt ctagaacgtc ctaaaaatgt cagaaatttg     120
ctgaaacttc cgaaaacagc cggaagttta caaaagctcc catacatttt cagaacttac     180
ttcaatattc tccatatcca tattttttaa aaatggctgt gcattaagct catcgtctat     240
taaactaaaa gaggtcatat tatatttagt ttccaatgcc aaaaactccc tatcccaggt     300
tttcacaaaa atatgtgaaa gactgaggaa atcttaaaaa taaacgtcca actttcatag     360 caccectctg atctttgaca atttttttaga tagagctaaa gatattactg aaaacatttt     420
atgatggttt tttaaaatta tgtatgtttt catgtctgag ttactagttt tccattacaa     480
aaacttaatt ctgatgtgac atttatgaaa attgccgacc attgcaataa aaagacacaa     540
taatttgaat aacaatgacc tcaatatgat aacattttca aggaggctat agcaaaaacg     600
```

```
ttattgtcgt tatacaggat cactagctca gtgcatttaa tagttggtca gtgactttat    660
ttttcagtca gtgcgcacat ctcgccccat gttccatact ggcaatctgc actcaacagt    720
tttattcttc attaatgcac gtaaacaaat gatgacggcc cgactcgttg aaaagggata    780
cctcctattt ctctactacc tctactctct atacCctcct tcttggccgc ggactaggtt    840
tcctcttcct cctttTcacc ctgctcaggg ttgacacact ttatcgattc tattaattag    900
ctctttcacc ttttttgtga catttttaaa tattaaatta agttatttga acgtttcaga    960
tgccttccac aaggagacaa caggagggcg gaggtgcaga tgcggaaaca catgtaagtt   1020
atttagacat tttatttttc tcaagaacta aattgttaaa attgctacaa tgcattgttt   1080
cagaccgttt acggtacaaa tctgataaca atcggaata gccaagaaga cgaaaatgtt    1140
gtggaagaag cggagctgaa atacggagca tctcacgtta ttcatctatt tgtgccggtg   1200
tcactatgca tggctctggt tgttttTacg atgaacacga ttacgtTTTa tagtcaaaac   1260
aatggaaggc atttgtaagt tttctaaaga attgattgat taaaaatatt tgatttgttt   1320
tatcaatttg catctgtgca atcgcactct ttgtcagtgc aaaataattt ttggtcagtg   1380
caaaataatt tttggtcagt gcattggtat tatggtcagt gcatttgcaa gtctgagctt   1440
taactatttt cgtggttTTa atTTtactca attttctatc aatatttctt tggaaaaaag   1500
ttgaagattt actctggaaa tttcgaaata aactgtaaat ggaaaaatca atcaacacaa   1560
actttgaatt attttcagac tatacactcc ttttgtccgg aaacagaca gtatcgttga    1620 gaagggattg atgtcacttg gaaatgctct cgtcatgttg tgcgtggtcg ttctgatgac   1680
agttctgctg attgttttct ataaatacaa gtttTataag cttattcatg gatggcttat   1740
tgtcagcagt tttcttcttc ttttcctatt cactacaatc tatgtgcagt aagttgatat   1800
attactattc cataaaaat atcaatgttg cagagaagtt ctgaaaagtt tcgatgtgtc    1860
tcccagcgca ctattggttt tgtttggact gggtaactat ggagttctcg aatgatgtg    1920 tatacattgg aaaggtccat tgcgtctgca acagttctac cttattacaa tgtctgcact   1980
aatggctctg gtctttatca agtacctacc agaatggact gtgtggtttg tgctgtttgt   2040
tatctcggtt tgggatctgg ttgccgtgct cacaccaaaa ggaccattga gatatttggt   2100
ggaaactgca caggagagaa acgagccaat tttcccggcg ctgatttatt cgtgtaagtt   2160
tcctaattta tggaattaat attcatgacg tttcaaattc taaaacattt tcagctggag   2220
tcatctatcc ctacgttctt gttactgcag ttgaaaacac gacagacccc cgtgaaccga   2280
cgtcgtcaga ctcaaatagt gagtatcacc taaaattttc gaatttttat tccaaaacta   2340
atttcagctt ctacagcttt tcctggagag gcgagttgtt catctgaaac gccaaaacgg   2400 ccaaagtga acgaattcc tcaaaaagtg caaatcgaat cgaatactac agcttcaacg    2460
acacaaaact ctggagtaag ggtggaacgg gagctagctg ctgagagacc aactgtacaa   2520
gacgccaatt ttcacaggca cgaagaggaa gagagtgagt gaaaacgtg ctgaaaaagg    2580 gcaaaggggg atgtattttc gcaaattTTa ctcgaactTT ctcacttcta actcaaatgt   2640
tttttcttga cagcacaaaa cgaaatatt gccgtctacg ttcggtatcg aaataccccc    2700
tgcaatTTTc attcgttttt ttttcactgt ttcatTTTTT ctcaactTTT gaagagcaat   2760
gccgcccact cagctgaata tattttgttc atttaaagtt caaaactttt cagttaatag   2820
attcaagaaa gatctcaaat aaacttgcaa gcttgccact tgcgctagtc acgaaaaaaa   2880
ggatttcttc aataaccctc tgttcatatt tttttTaaca ataatttttc atctcttcat   2940
```

-continued

| | |
|---|---|
| attttgatat gttttgcaac aaaaaaatga ttgcaggagg tgtgaaactt ggtctgggcg | 3000 |
| acttcatttt ctactctgtt ctcctcggca aggcttcatc gtactttgac tggaacacga | 3060 |
| ctatcgcttg ttatgtggcc attcttatcg gtctctgctt cactcttgtc ctgctcgccg | 3120 |
| tcttcaaacg agcactcccg gctctgccaa tttccatttt ctccggactc attttttact | 3180 |
| tttgtacccg ctggatcatc accccatttg ttacacaagt ctctcaaaag tgtttattat | 3240 |
| attaattctc tgtttttgcc atttctttgc atcatcaact tttcgattat atcttgagcg | 3300 |
| atctcaaagc tttattttac atacctattt attttttgaac tttgtcattt aagttatata | 3360 |
| aataatttat taaacgtttc tgctattttt ttttcattat tcttgatcct atgcttacag | 3420 |
| gtgcttcaga ttcctttttt gctttagaag tatcatcaaa gtgtttattt aaagtatttc | 3480 |
| agatgttttc ttcacgtcat attttatcaa acgttcgtcc aataataaag gtaagttaag | 3540 |
| gtaagtagac atattcagtt ccaaagttgg aaaattagtg aaacaacatt ttttataaag | 3600 |
| tagttgaaat acatagtgaa tttcttgtta aattaaaaat gtagcagaag ttgggataaa | 3660 |
| ttaaaaattt tactttcaga atctagacct gaccagaggg ttttccgaca ggaaaacaaa | 3720 |
| atattttgac ttgaatgacc ttatcaaaac tgtaaatgtt acctacaaga ctggagtaaa | 3780 |
| cctggaggaa accacaactg tcgagtcaaa atatgtagta agttttttg ttttttttt | 3840 |
| caaaaaatta acctttaaat tattgcttca ggatgtcaca ccttcatcaa acacaaaagg | 3900 |
| aaccgtagtg acactatcag gatcacctgg tacacataac gattttaagt acatgaaatc | 3960 |
| gttttttgag cagaagaaaa ttcgcttaat ttgcaccaac tatcccgggt cggaatttgt | 4020 |
| aacgggtggc ttgcacaata gttatacaaa tcaagatcga aattcgtaca tgaaaagttt | 4080 |
| aatggaaaca ctggagttga aaaatgtaaa ccgacttatt ataatgggac actcgag | 4137 |

<210> SEQ ID NO 2
<211> LENGTH: 2764
<212> TYPE: DNA
<213> ORGANISM: Caenorhabditis elegans

<400> SEQUENCE: 2

| | |
|---|---|
| tgggacaggc agctccgggg tccgcggttt cacatcggaa acaaaacagc ggctggtctg | 60 |
| gaaggaacct gagctacgag ccgcggcggc agcggggcgg cggggaagcg tatacctaat | 120 |
| ctgggagcct gcaagtgaca acagcctttg cggtccttag acagcttggc ctggaggaga | 180 |
| acacatgaaa gaagaacct caagaggctt tgttttctgt gaaacagtat ttctatacag | 240 |
| ttgctccaat gacagagtta cctgcaccgt tgtcctactt ccagaatgca cagatgtctg | 300 |
| aggacaacca cctgagcaat actgtacgta gccagaatga aatagagaa cggcaggagc | 360 |
| acaacgacag acggagcctt ggccaccctg agccattatc taatggacga ccccagggta | 420 |
| actcccggca gtggtggag caagatgagg aagaagatga ggagctgaca ttgaaatatg | 480 |
| gcgccaagca tgtgatcatg ctctttgtcc ctgtgactct ctgcatggtg gtggtcgtgg | 540 |
| ctaccattaa gtcagtcagc ttttatacccc ggaaggatgg gcagctaatc tatacccccat | 600 |
| tcacagaaga taccgagact gtgggccaga gagccctgca ctcaattctg aatgctgcca | 660 |
| tcatgatcag tgtcattgtt gtcatgacta tcctcctggt ggttctgtat aaatacaggt | 720 |
| gctataaggt catccatgcc tggcttatta tatcatctct attgttgctg ttctttttt | 780 |
| cattcattta cttgggggaa gtgtttaaaa cctataacgt tgctgtggac tacattactg | 840 |
| ttgcactcct gatctggaat tttggtgtgg tgggaatgat ttccattcac tggaaaggtc | 900 |
| cacttcgact ccagcaggca tatctcatta tgattagtgc cctcatggcc ctggtgttta | 960 |

```
tcaagtacct cccctgaatgg actgcgtggc tcatcttggc tgtgatttca gtatatgatt    1020
tagtggctgt tttgtgtccg aaaggtccac ttcgtatgct ggttgaaaca gctcaggaga    1080
gaaatgaaac gcttttttcca gctctcattt actcctcaac aatggtgtgg ttggtgaata   1140
tggcagaagg agacccggaa gctcaaagga gagtatccaa aaattccaag tataatgcag    1200
aaagcacaga aagggagtca caagacactg ttgcagagaa tgatgatggc gggttcagtg    1260
aggaatggga agcccagagg gacagtcatc tagggcctca tcgctctaca cctgagtcac    1320
gagctgctgt ccaggaactt tccagcagta tcctcgctgg tgaagaccca gaggaaaggg    1380 gagtaaaaact tggatttggga gatttcattt tctacagtgt tctggttggt aaagcctcag   1440
caacagccag tggagactgg aacacaacca tagcctgttt cgtagccata ttaattggtt    1500
tgtgccttac attattactc cttgccattt tcaagaaagc attgccagct cttccaatct    1560
ccatcacctt tgggcttgtt ttctactttg ccacagatta tcttgtacag ccttttatgg    1620
accaattagc attccatcaa ttttatatct agcatatttg cggttagaat cccatggatg    1680
tttcttcttt gactataacc aaatctgggg aggacaaagg tgattttcct gtgtccacat    1740
ctaacaaagt caagattccc ggctggactt ttgcagcttc cttccaagtc ttcctgacca    1800
ccttgcacta ttggactttg gaaggaggtg cctatagaaa acgattttga acatacttca    1860
tcgcagtgga ctgtgtccct cggtgcagaa actaccagat ttgagggacg aggtcaagga    1920
gatatgatag gcccggaagt tgctgtgccc catcagcagc ttgacgcgtg gtcacaggac    1980
gatttcactg acactgcgaa ctctcaggac taccggttac caagaggtta ggtgaagtgg    2040
tttaaaccaa acggaactct tcatcttaaa ctacacgttg aaaatcaacc caataattct    2100
gtattaactg aattctgaac ttttcaggag gtactgtgag gaagagcagg caccagcagc    2160
agaatgggga atggagaggt gggcaggggt tccagcttcc ctttgattt ttgctgcaga     2220 ctcatccttt ttaaatgaga cttgtttttcc cctctctttg agtcaagtca aatatgtaga    2280
ttgcctttgg caattcttct tctcaagcac tgacactcat taccgtctgt gattgccatt    2340
tcttcccaag gccagtctga acctgaggtt gctttatcct aaaagtttta acctcaggtt    2400
ccaaattcag taaatttttgg aaacagtaca gctatttctc atcaattctc tatcatgttg    2460
aagtcaaatt tggattttcc accaaattct gaatttgtag acatacttgt acgctcactt    2520
gcccccagat gcctcctctg tcctcattct tctctcccac acaagcagtc tttttctaca    2580
gccagtaagg cagctctgtc tggtagcaga tggtcccatt attctagggt cttactcttt    2640
gtatgatgaa aagaatgtgt tatgaatcgg tgctgtcagc cctgctgtca gaccttcttc    2700
cacagcaaat gagatgtatg cccaaagcgg tagaattaaa gaagagtaaa atggctgttg    2760
aagc                                                                 2764
```

<210> SEQ ID NO 3
<211> LENGTH: 467
<212> TYPE: PRT
<213> ORGANISM: Caenorhabditis elegans

<400> SEQUENCE: 3

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

```
Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
            130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
            210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
            245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
            290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
            370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
            435                 440                 445

Thr Asp Tyr Leu Val Gln Pro Phe Met Asp Gln Leu Ala Phe His Gln
450                 455                 460
```

Phe Tyr Ile
465

<210> SEQ ID NO 4
<211> LENGTH: 3148
<212> TYPE: DNA
<213> ORGANISM: Caenorhabditis elegans

<400> SEQUENCE: 4

| | | | | | |
|---|---|---|---|---|---|
| gaattcccgc | ggagcagcgt | gcgcggggcc | ccgggagacg | gcggcggtag | cggcgcgggc | 60 |
| agagcaagga | cgcggcggat | cccactcgca | cagcagcgca | ctcggtgccc | cgcgcagggt | 120 |
| cgcgatgctg | cccggtttgg | cactgctcct | gctggccgcc | tggacggctc | gggcgctgga | 180 |
| ggtacccact | gatggtaatg | ctggcctgct | ggctgaaccc | cagattgcca | tgttctgtgg | 240 |
| cagactgaac | atgcacatga | atgtccagaa | tgggaagtgg | gattcagatc | catcagggac | 300 |
| caaaacctgc | attgatacca | aggaaggcat | cctgcagtat | tgccaagaag | tctaccctga | 360 |
| actgcagatc | accaatgtgg | tagaagccaa | ccaaccagtg | accatccaga | actggtgcaa | 420 |
| gcggggccgc | aagcagtgca | agacccatcc | ccactttgtg | attccctacc | gctgcttagt | 480 |
| tggtgagttt | gtaagtgatg | cccttctcgt | tcctgacaag | tgcaaattct | acaccaggaa | 540 |
| gaggatggat | gtttgcgaaa | ctcatcttca | ctggcacacc | gtcgccaaag | agacatgcag | 600 |
| tgagaagagt | accaacttgc | atgactacgg | catgttgctg | ccctgcggaa | ttgacaagtt | 660 |
| ccgagggggta | gagtttgtgt | gttgcccact | ggctgaagaa | agtgacaatg | tggattctgc | 720 |
| tgatgcggag | gaggatgact | cggatgtctg | gtggggcgga | gcagacacag | actatgcaga | 780 |
| tgggagtgaa | gacaaagtag | tagaagtagc | agaggaggaa | gaagtggctg | aggtggaaga | 840 |
| agaagaagcc | gatgatgacg | aggacgatga | ggatggtgat | gaggtagagg | aagaggctga | 900 |
| ggaaccctac | gaagaagcca | cagagagaac | caccagcatt | gccaccacca | ccaccaccac | 960 |
| cacagagtct | gtggaagagg | tggttcgaga | ggtgtgctct | gaacaagccg | agacggggcc | 1020 |
| gtgccgagca | atgatctccc | gctggtactt | tgatgtgact | gaagggaagt | gtgccccatt | 1080 |
| cttttacggc | ggatgtggcg | gcaaccggaa | caactttgac | acagaagagt | actgcatggc | 1140 |
| cgtgtgtggc | agcgccattc | ctacaacagc | agccagtacc | cctgatgccg | ttgacaagta | 1200 |
| tctcgagaca | cctggggatg | agaatgaaca | tgcccatttc | cagaaagcca | aagagaggct | 1260 |
| tgaggccaag | caccgagaga | aatgtccca | ggtcatgaga | aatgggaag | aggcagaacg | 1320 |
| tcaagcaaag | aacttgccta | agctgataaa | gaaggcagtt | atccagcatt | tccaggagaa | 1380 |
| agtggaatct | ttggaacagg | aagcagccaa | cgagagacag | cagctggtgg | agacacacat | 1440 |
| ggccagagtg | gaagccatgc | tcaatgaccg | ccgccgcctg | gccctggaga | actacatcac | 1500 |
| cgctctgcag | gctgttcctc | ctcggcctcg | tcacgtgttc | aatatgctaa | agaagtatgt | 1560 |
| ccgcgcagaa | cagaaggaca | gacagcacac | cctaaagcat | ttcgagcatg | tgcgcatggt | 1620 |
| ggatcccaag | aaagccgctc | agatccggtc | ccaggttatg | acacacctcc | gtgtgattta | 1680 |
| tgagcgcatg | aatcagtctc | tctccctgct | ctacaacgtg | cctgcagtgg | ccgaggagat | 1740 |
| tcaggatgaa | gttgatgagc | tgcttcagaa | agagcaaaac | tattcagatg | acgtcttggc | 1800 |
| caacatgatt | agtgaaccaa | ggatcagtta | cggaaacgat | gctctcatgc | catctttgac | 1860 |
| cgaaacgaaa | accaccgtgg | agctccttcc | cgtgaatgga | gagttcagcc | tggacgatct | 1920 |
| ccagccgtgg | cattcttttg | gggctgactc | tgtgccagcc | aacacagaaa | acgaagttga | 1980 |
| gcctgttgat | gcccgccctg | ctgccgaccg | aggactgacc | actcgaccag | gttctgggtt | 2040 |

-continued

```
gacaaatatc aagacggagg agatctctga agtgaagatg gatgcagaat ccgacatga       2100 ctcaggatat gaagttcatc atcaaaaatt ggtgttcttt gcagaagatg tgggttcaaa       2160
caaaggtgca atcattggac tcatggtggg cggtgttgtc atagcgacag tgatcgtcat       2220
caccttggtg atgctgaaga agaaacagta cacatccatt catcatggtg tggtggaggt       2280
tgacgccgct gtcaccccag aggagcgcca cctgtccaag atgcagcaga acggctacga       2340
aaatccaacc tacaagttct tgagcagat gcagaactag acccccgcca cagcagcctc        2400
tgaagttgga cagcaaaacc attgcttcac tacccatcgg tgtccattta tagaataatg       2460
tgggaagaaa caaacccgtt ttatgattta ctcattatcg ccttttgaca gctgtgctgt       2520
aacacaagta gatgcctgaa cttgaattaa tccacacatc agtaatgtat tctatctctc       2580
tttacatttt ggtctctata ctacattatt aatgggtttt gtgtactgta aagaatttag       2640
ctgtatcaaa ctagtgcatg aatagattct ctcctgatta tttatcacat agccccttag       2700
ccagttgtat attattcttg tggtttgtga cccaattaag tcctacttta catatgcttt       2760
aagaatcgat gggggatgct tcatgtgaac gtgggagttc agctgcttct cttgcctaag       2820 tattccttc ctgatcacta tgcattttaa agttaaacat ttttaagtat ttcagatgct        2880
ttagagagat tttttttcca tgactgcatt ttactgtaca gattgctgct tctgctatat       2940
ttgtgatata ggaattaaga ggatacacac gtttgtttct tcgtgcctgt tttatgtgca       3000
cacattaggc attgagactt caagcttttc ttttttgtc cacgtatctt tgggtctttg        3060
ataaagaaaa gaatccctgt tcattgtaag cacttttacg gggcgggtgg ggagggtgc        3120 tctgctggtc ttcaattacc aagaattc                                          3148
```

<210> SEQ ID NO 5
<211> LENGTH: 751
<212> TYPE: PRT
<213> ORGANISM: Caenorhabditis elegans

<400> SEQUENCE: 5

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

-continued

```
Asp Lys Phe Arg Gly Val Glu Phe Val Cys Cys Pro Leu Ala Glu Glu
            180                 185                 190

Ser Asp Asn Val Asp Ser Ala Asp Glu Glu Asp Asp Ser Asp Val
            195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Ala Thr Glu Arg Thr Thr Ser Ile
            260                 265                 270

Ala Thr Thr Thr Thr Thr Thr Glu Ser Val Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
            355                 360                 365

His Ala His Phe Gln Lys Ala Lys Glu Arg Leu Glu Ala Lys His Arg
            370                 375                 380

Glu Arg Met Ser Gln Val Met Arg Glu Trp Glu Ala Glu Arg Gln
385                 390                 395                 400

Ala Lys Asn Leu Pro Lys Ala Asp Lys Lys Ala Val Ile Gln His Phe
                405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
                485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
```

-continued

```
                    595                 600                 605
Ser Val Pro Ala Asn Thr Glu Asn Glu Val Glu Pro Val Asp Ala Arg
    610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
                660                 665                 670

Ala Glu Asp Val Gly Ser Asn Lys Gly Ala Ile Ile Gly Leu Met Val
            675                 680                 685

Gly Gly Val Val Ile Ala Thr Val Ile Val Ile Thr Leu Val Met Leu
690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
                740                 745                 750

<210> SEQ ID NO 6
<211> LENGTH: 20
<212> TYPE: DNA
<213> ORGANISM: Caenorhabditis elegans

<400> SEQUENCE: 6
aatcggatcc atggcttcac                                                 20

<210> SEQ ID NO 7
<211> LENGTH: 23
<212> TYPE: DNA
<213> ORGANISM: Caenorhabditis elegans

<400> SEQUENCE: 7
ccgaattctg tccgaaaggt cca                                             23

<210> SEQ ID NO 8
<211> LENGTH: 26
<212> TYPE: DNA
<213> ORGANISM: Caenorhabditis elegans

<400> SEQUENCE: 8
ccggatccct aggttgtgtt ccagtc                                          26
```

What is claimed is:

1. An isolated DNA molecule comprising:
   the promoter of the sel-12 gene from *C. elegans*, wherein said promoter comprises nucleotides 1-959 as set forth in SEQ ID NO: 1,
   the promoter being operably linked to a heterologous DNA sequence, the DNA sequence encoding a protein of interest.

2. The DNA molecule of claim 1 wherein the heterologous DNA sequence comprises the nucleotide sequence of SEQ ID NOs:2 or 4 or encodes the amino acid sequence of SEQ ID NOs:3 or 5.

3. A vector comprising a DNA molecule of claim 1.

4. A vector of claim 3, which further comprises a selectable marker.

5. A vector comprising a DNA molecule of claim 2.

6. A vector of claim 5, which further comprises a selectable marker.

7. A cultured cell transformed with at least one DNA molecule of claim 1.

8. The cell of claim 7, which is a prokaryotic cell.

9. The cell of claim 7, which is a eukaryotic cell.

10. A composition comprising a DNA molecule of claim 1, and a pharmaceutically acceptable carrier.

* * * * *